US010675019B2

(12) United States Patent
Westling et al.

(10) Patent No.: US 10,675,019 B2
(45) Date of Patent: Jun. 9, 2020

(54) MEDICAL IMPLANT DELIVERY SYSTEM AND RELATED METHODS

(71) Applicant: Rotation Medical, Inc., Plymouth, MN (US)

(72) Inventors: Thomas A. Westling, Orono, MN (US); Nathaniel Zenz-Olson, Blaine, MN (US); Nathaniel Tran, Lakeville, MN (US)

(73) Assignee: Rotation Medical, Inc., Plymouth, MN (US)

( * ) Notice: Subject to any disclaimer, the term of this patent is extended or adjusted under 35 U.S.C. 154(b) by 1241 days.

(21) Appl. No.: 14/931,423

(22) Filed: Nov. 3, 2015

(65) Prior Publication Data

US 2016/0120538 A1    May 5, 2016

Related U.S. Application Data

(60) Provisional application No. 62/074,982, filed on Nov. 4, 2014.

(51) Int. Cl.
*A61B 17/068* (2006.01)
*A61B 17/064* (2006.01)
*A61B 17/00* (2006.01)

(52) U.S. Cl.
CPC ...... *A61B 17/0682* (2013.01); *A61B 17/0642* (2013.01); *A61B 17/068* (2013.01); *A61B 2017/00367* (2013.01)

(58) Field of Classification Search
CPC .............. A61B 17/068; A61B 17/0682; A61B 17/0642; A61B 17/10; A61B 17/0469;
(Continued)

(56) References Cited

U.S. PATENT DOCUMENTS 511,238 A    12/1893   Hieatzman et al.
765,793 A     7/1904   Ruckel
(Continued)

FOREIGN PATENT DOCUMENTS

AU    2010256474 B2    12/2010
CA    2390508 A1        5/2001
(Continued)

OTHER PUBLICATIONS

Notification of Transmittal of the International Search Report and the Written Opinion of the International Searching Authority, or the Declaration, dated Jan. 20, 2016, 15 pages.
(Continued)

*Primary Examiner* — David W Bates
*Assistant Examiner* — Marcela I Shirsat
(74) *Attorney, Agent, or Firm* — Seager, Tufte & Wickhem LLP

(57) ABSTRACT

A fastener delivery tool may comprise a sheath assembly having at least one position retention member proximate a distal end of the sheath assembly, and a handle assembly coupled to a proximal end of the sheath assembly, the handle assembly comprising a housing, a trigger handle, and an insert connector. An external force applied to the trigger handle may cause displacement of the trigger handle relative to a rest position, and displacement of the trigger handle from the rest position within a first displacement range may impart a first amount of force on the insert connector relative to the applied external force and displacement of the trigger handle from the rest position within a second displacement range may impart a second amount of force on the insert connector relative to the applied external force, with the first amount of force being greater than the second amount of force.

20 Claims, 28 Drawing Sheets

(58) Field of Classification Search
CPC .. A61B 2017/00367; A61B 2017/0409; A61B 2017/00668; B25C 5/0214; B25C 5/0285; B25C 5/1617; B25C 5/1627; B25C 5/06; B25C 5/10; B25C 5/11
USPC .................. 606/142–143, 329, 75, 138, 219; 227/175.1, 175.3, 176.1–181.1, 901–902
See application file for complete search history.

(56) References Cited

U.S. PATENT DOCUMENTS

| | | |
|---|---|---|
| 1,728,316 A | 9/1929 | Von Wachenfeldt |
| 1,855,546 A | 4/1932 | File |
| 1,868,100 A | 7/1932 | Goodstein |
| 1,910,688 A | 5/1933 | Goodstein |
| 1,940,351 A | 12/1933 | Howard |
| 2,034,785 A | 3/1936 | Wappler |
| 2,075,508 A | 3/1937 | Davidson |
| 2,131,321 A | 9/1938 | Hart |
| 2,154,688 A | 4/1939 | Matthews et al. |
| 2,158,242 A | 5/1939 | Maynard |
| 2,199,025 A | 4/1940 | Conn |
| 2,201,610 A | 5/1940 | Dawson, Jr. |
| 2,254,620 A | 9/1941 | Miller |
| 2,277,931 A | 3/1942 | Moe |
| 2,283,814 A | 5/1942 | La Place |
| 2,316,297 A | 4/1943 | Southerland et al. |
| 2,390,508 A | 12/1945 | Carleton |
| 2,397,240 A | 3/1946 | Butler |
| 2,421,193 A | 5/1947 | Gardner |
| 2,571,813 A | 10/1951 | Austin |
| 2,630,316 A | 3/1953 | Foster |
| 2,684,070 A | 7/1954 | Kelsey |
| 2,744,251 A | 5/1956 | Vollmer |
| 2,790,341 A | 4/1957 | Keep et al. |
| 2,817,339 A | 12/1957 | Sullivan |
| 2,825,162 A | 3/1958 | Flood |
| 2,881,762 A | 4/1959 | Lowrie |
| 2,910,067 A | 10/1959 | White |
| 3,068,870 A | 12/1962 | Levin |
| 3,077,812 A | 2/1963 | Dietrich |
| 3,103,666 A | 9/1963 | Bone |
| 3,120,377 A | 2/1964 | Lipschultz et al. |
| 3,123,077 A | 3/1964 | Alcamo |
| 3,209,754 A | 10/1965 | Brown |
| 3,221,746 A | 12/1965 | Noble |
| 3,470,834 A | 10/1969 | Bone |
| 3,527,223 A | 9/1970 | Shein |
| 3,570,497 A | 3/1971 | Lemole |
| 3,577,837 A | 5/1971 | Bader, Jr. |
| 3,579,831 A | 5/1971 | Stevens et al. |
| 3,643,851 A | 2/1972 | Green et al. |
| 3,687,138 A | 8/1972 | Jarvik |
| 3,716,058 A | 2/1973 | Tanner, Jr. |
| 3,717,294 A | 2/1973 | Green |
| 3,740,994 A | 6/1973 | DeCarlo, Jr. |
| 3,757,629 A | 9/1973 | Schneider |
| 3,777,538 A | 12/1973 | Weatherly et al. |
| 3,837,555 A | 9/1974 | Green |
| 3,845,772 A | 11/1974 | Smith |
| 3,875,648 A | 4/1975 | Bone |
| 3,955,581 A * | 5/1976 | Spasiano .............. A61B 17/068 227/175.1 |
| 3,960,147 A | 6/1976 | Murray |
| 3,976,079 A | 8/1976 | Samuels et al. |
| 4,014,492 A | 3/1977 | Rothfuss |
| 4,127,227 A | 11/1978 | Green |
| 4,259,959 A | 4/1981 | Walker |
| 4,263,903 A | 4/1981 | Griggs |
| 4,265,226 A | 5/1981 | Cassimally |
| 4,317,451 A | 3/1982 | Cerwin et al. |
| 4,400,833 A | 8/1983 | Kurland |
| 4,422,567 A | 12/1983 | Haynes |
| 4,454,875 A | 6/1984 | Pratt et al. |
| 4,480,641 A | 11/1984 | Failla et al. |
| 4,485,816 A | 12/1984 | Krumme |
| 4,526,174 A | 7/1985 | Froehlich |
| 4,549,545 A | 10/1985 | Levy |
| 4,570,623 A | 2/1986 | Ellison et al. |
| 4,586,197 A | 5/1986 | Hubbard |
| 4,595,007 A | 6/1986 | Mericle |
| 4,610,251 A | 9/1986 | Kumar |
| 4,624,254 A | 11/1986 | McGarry et al. |
| 4,627,437 A | 12/1986 | Bedi et al. |
| 4,632,100 A | 12/1986 | Somers et al. |
| 4,635,634 A | 1/1987 | Santos |
| 4,635,637 A | 1/1987 | Schreiber |
| 4,669,473 A | 6/1987 | Richards et al. |
| 4,696,300 A | 9/1987 | Anderson |
| 4,719,917 A | 1/1988 | Barrows et al. |
| 4,738,255 A | 4/1988 | Goble et al. |
| 4,741,330 A | 5/1988 | Hayhurst |
| 4,762,260 A | 8/1988 | Richards et al. |
| 4,799,495 A | 1/1989 | Hawkins et al. |
| 4,809,695 A | 3/1989 | Gwathmey et al. |
| 4,851,005 A | 7/1989 | Hunt et al. |
| 4,858,608 A | 8/1989 | McQuilkin |
| 4,884,572 A | 12/1989 | Bays et al. |
| 4,887,601 A | 12/1989 | Richards |
| 4,924,866 A | 5/1990 | Yoon |
| 4,930,674 A | 6/1990 | Barak |
| 4,968,315 A | 11/1990 | Gattuma |
| 4,976,715 A | 12/1990 | Bays et al. |
| 4,994,073 A | 2/1991 | Green |
| 4,997,436 A | 3/1991 | Oberlander |
| 5,002,563 A | 3/1991 | Pyka et al. |
| 5,013,316 A | 5/1991 | Goble et al. |
| 5,015,249 A | 5/1991 | Nakao et al. |
| 5,037,422 A | 8/1991 | Hayhurst et al. |
| 5,041,129 A | 8/1991 | Hayhurst et al. |
| 5,046,513 A | 9/1991 | Gattuma et al. |
| 5,053,047 A | 10/1991 | Yoon |
| 5,059,206 A | 10/1991 | Winters |
| 5,062,563 A | 11/1991 | Green et al. |
| 5,100,417 A | 3/1992 | Cerier et al. |
| 5,102,421 A | 4/1992 | Anspach, Jr. |
| 5,116,357 A | 5/1992 | Eberbach |
| 5,122,155 A | 6/1992 | Eberbach |
| 5,123,913 A | 6/1992 | Wilk et al. |
| RE34,021 E | 8/1992 | Mueller et al. |
| 5,141,515 A | 8/1992 | Eberbach |
| 5,141,520 A | 8/1992 | Goble et al. |
| 5,156,609 A | 10/1992 | Nakao et al. |
| 5,156,616 A | 10/1992 | Meadows et al. |
| 5,167,665 A | 12/1992 | McKinney |
| 5,171,259 A | 12/1992 | Inoue |
| 5,174,295 A | 12/1992 | Christian et al. |
| 5,174,487 A | 12/1992 | Rothfuss et al. |
| 5,176,682 A | 1/1993 | Chow |
| 5,176,692 A | 1/1993 | Wilk et al. |
| 5,203,787 A | 4/1993 | Noblitt et al. |
| 5,217,472 A | 6/1993 | Green et al. |
| 5,224,946 A | 7/1993 | Hayhurst et al. |
| 5,242,457 A | 9/1993 | Akopov et al. |
| 5,246,441 A | 9/1993 | Ross et al. |
| 5,251,642 A | 10/1993 | Handlos |
| 5,261,914 A | 11/1993 | Warren |
| 5,269,753 A | 12/1993 | Wilk |
| 5,269,783 A | 12/1993 | Sander |
| 5,282,829 A | 2/1994 | Hermes |
| 5,289,963 A | 3/1994 | McGarry et al. |
| 5,290,217 A | 3/1994 | Campos |
| 5,304,187 A | 4/1994 | Green et al. |
| 5,333,624 A | 8/1994 | Tovey |
| 5,342,396 A | 8/1994 | Cook |
| 5,350,400 A | 9/1994 | Esposito et al. |
| 5,352,229 A | 10/1994 | Goble et al. |
| 5,354,292 A | 10/1994 | Braeuer et al. |
| 5,364,408 A | 11/1994 | Gordon |
| 5,366,460 A | 11/1994 | Eberbach |
| 5,370,650 A | 12/1994 | Tovey et al. |
| 5,372,604 A | 12/1994 | Trott |
| 5,380,334 A | 1/1995 | Torrie et al. |
| 5,383,477 A | 1/1995 | DeMatteis |

(56) References Cited

U.S. PATENT DOCUMENTS

| | | |
|---|---|---|
| 5,397,332 A | 3/1995 | Kammerer et al. |
| 5,403,326 A | 4/1995 | Harrison et al. |
| 5,405,360 A | 4/1995 | Tovey |
| 5,411,522 A | 5/1995 | Trott |
| 5,411,523 A | 5/1995 | Goble |
| 5,417,691 A | 5/1995 | Hayhurst |
| 5,417,712 A | 5/1995 | Whittaker et al. |
| 5,425,490 A | 6/1995 | Goble et al. |
| 5,439,468 A | 8/1995 | Schulze et al. |
| 5,441,502 A | 8/1995 | Bartlett |
| 5,441,508 A | 8/1995 | Gazielly et al. |
| 5,456,720 A | 10/1995 | Schultz et al. |
| 5,458,579 A | 10/1995 | Chodorow et al. |
| 5,464,403 A | 11/1995 | Kieturakis et al. |
| 5,478,354 A | 12/1995 | Tovey et al. |
| 5,486,197 A | 1/1996 | Le et al. |
| 5,497,933 A | 3/1996 | DeFonzo et al. |
| 5,500,000 A | 3/1996 | Feagin et al. |
| 5,501,695 A | 3/1996 | Anspach, Jr. et al. |
| 5,503,623 A | 4/1996 | Tilton, Jr. |
| 5,505,735 A | 4/1996 | Li |
| 5,507,754 A | 4/1996 | Green et al. |
| 5,520,185 A | 5/1996 | Soni et al. |
| 5,520,700 A | 5/1996 | Beyar et al. |
| 5,522,817 A | 6/1996 | Sander et al. |
| 5,538,297 A | 7/1996 | Mc Naughton et al. |
| 5,545,180 A | 8/1996 | Le et al. |
| 5,548,893 A | 8/1996 | Koelfgen et al. |
| 5,560,532 A | 10/1996 | DeFonzo et al. |
| 5,562,689 A | 10/1996 | Green et al. |
| 5,569,306 A | 10/1996 | Thal |
| 5,582,616 A | 12/1996 | Bolduc et al. |
| 5,584,835 A | 12/1996 | Greenfield |
| 5,593,421 A | 1/1997 | Bauer |
| 5,601,573 A | 2/1997 | Fogelberg et al. |
| 5,618,314 A | 4/1997 | Harwin et al. |
| 5,622,257 A | 4/1997 | Deschenes et al. |
| 5,628,751 A | 5/1997 | Sander et al. |
| 5,643,319 A | 7/1997 | Green et al. |
| 5,643,321 A | 7/1997 | McDevitt |
| 5,647,874 A | 7/1997 | Hayhurst |
| 5,649,963 A | 7/1997 | McDevitt |
| 5,662,683 A | 9/1997 | Kay |
| 5,667,513 A | 9/1997 | Torrie et al. |
| 5,674,245 A | 10/1997 | Ilgen |
| 5,681,342 A | 10/1997 | Benchetrit |
| 5,702,215 A | 12/1997 | Li |
| 5,713,903 A | 2/1998 | Sander et al. |
| 5,720,753 A | 2/1998 | Sander et al. |
| 5,725,541 A | 3/1998 | Anspach, III et al. |
| 5,741,282 A | 4/1998 | Anspach, III et al. |
| 5,766,246 A | 6/1998 | Mulhauser et al. |
| 5,782,864 A | 7/1998 | Lizardi |
| 5,797,909 A | 8/1998 | Michelson |
| 5,797,931 A | 8/1998 | Bito et al. |
| 5,797,963 A | 8/1998 | McDevitt |
| 5,807,403 A | 9/1998 | Beyar et al. |
| 5,830,221 A | 11/1998 | Stein et al. |
| 5,833,700 A | 11/1998 | Fogelberg et al. |
| 5,836,961 A | 11/1998 | Kieturakis et al. |
| 5,868,762 A | 2/1999 | Cragg et al. |
| 5,873,891 A | 2/1999 | Sohn |
| 5,885,258 A | 3/1999 | Sachdeva et al. |
| 5,885,294 A | 3/1999 | Pedlick et al. |
| 5,893,856 A | 4/1999 | Jacob et al. |
| 5,904,696 A | 5/1999 | Rosenman |
| 5,919,184 A | 7/1999 | Tilton, Jr. |
| 5,922,026 A | 7/1999 | Chin |
| 5,928,244 A | 7/1999 | Tovey et al. |
| 5,948,000 A | 9/1999 | Larsen et al. |
| 5,957,939 A | 9/1999 | Heaven et al. |
| 5,957,953 A | 9/1999 | Dipoto et al. |
| 5,968,044 A | 10/1999 | Nicholson et al. |
| 5,980,557 A | 11/1999 | Iserin et al. |
| 5,989,265 A | 11/1999 | Bouquet De La Joliniere et al. |
| 5,997,552 A | 12/1999 | Person et al. |
| 6,063,088 A | 5/2000 | Winslow |
| 6,156,045 A | 12/2000 | Ulbrich et al. |
| 6,179,840 B1 | 1/2001 | Bowman |
| 6,193,731 B1 | 2/2001 | Oppelt et al. |
| 6,193,733 B1 | 2/2001 | Adams |
| 6,245,072 B1 | 6/2001 | Zdeblick et al. |
| 6,302,885 B1 | 10/2001 | Essiger |
| 6,312,442 B1 | 11/2001 | Kieturakis et al. |
| 6,315,789 B1 | 11/2001 | Cragg |
| 6,318,616 B1 | 11/2001 | Pasqualucci et al. |
| 6,322,563 B1 | 11/2001 | Cummings et al. |
| 6,325,805 B1 | 12/2001 | Ogilvie et al. |
| 6,342,057 B1 | 1/2002 | Brace et al. |
| 6,387,113 B1 | 5/2002 | Hawkins et al. |
| 6,391,333 B1 | 5/2002 | Li et al. |
| 6,413,274 B1 | 7/2002 | Pedros |
| 6,425,900 B1 | 7/2002 | Knodel et al. |
| 6,436,110 B2 | 8/2002 | Bowman et al. |
| 6,447,522 B2 | 9/2002 | Gambale et al. |
| 6,447,524 B1 | 9/2002 | Knodel et al. |
| 6,478,803 B1 | 11/2002 | Kapec et al. |
| 6,482,178 B1 | 11/2002 | Andrews et al. |
| 6,482,210 B1 | 11/2002 | Skiba et al. |
| 6,506,190 B1 | 1/2003 | Walshe |
| 6,511,499 B2 | 1/2003 | Schmieding et al. |
| 6,517,564 B1 | 2/2003 | Grafton et al. |
| 6,524,316 B1 | 2/2003 | Nicholson et al. |
| 6,527,795 B1 | 3/2003 | Lizardi |
| 6,530,933 B1 | 3/2003 | Yeung et al. |
| 6,540,769 B1 | 4/2003 | Miller, III |
| 6,551,333 B2 | 4/2003 | Kuhns et al. |
| 6,554,852 B1 | 4/2003 | Oberlander |
| 6,569,186 B1 | 5/2003 | Winters et al. |
| 6,575,976 B2 | 6/2003 | Grafton |
| 6,599,286 B2 | 7/2003 | Campin et al. |
| 6,599,289 B1 | 7/2003 | Bojarski et al. |
| 6,620,185 B1 | 9/2003 | Harvie et al. |
| 6,626,930 B1 | 9/2003 | Allen et al. |
| 6,629,988 B2 | 10/2003 | Weadock |
| 6,638,297 B1 | 10/2003 | Huitema |
| 6,648,893 B2 | 11/2003 | Dudasik |
| 6,666,872 B2 | 12/2003 | Barreiro et al. |
| 6,673,094 B1 | 1/2004 | McDevitt et al. |
| 6,685,728 B2 | 2/2004 | Sinnott et al. |
| 6,692,506 B1 | 2/2004 | Ory et al. |
| 6,723,099 B1 | 4/2004 | Goshert |
| 6,726,704 B1 | 4/2004 | Loshakove et al. |
| 6,726,705 B2 | 4/2004 | Peterson et al. |
| 6,740,100 B2 | 5/2004 | Demopulos et al. |
| 6,746,472 B2 | 6/2004 | Frazier et al. |
| 6,764,500 B1 | 7/2004 | Muijs Van De Moer et al. |
| 6,770,073 B2 | 8/2004 | McDevitt et al. |
| 6,779,701 B2 | 8/2004 | Bailly et al. |
| 6,800,081 B2 | 10/2004 | Parodi |
| 6,835,206 B2 | 12/2004 | Jackson |
| 6,849,078 B2 | 2/2005 | Durgin et al. |
| 6,887,259 B2 | 5/2005 | Lizardi |
| 6,926,723 B1 | 8/2005 | Mulhauser et al. |
| 6,932,834 B2 | 8/2005 | Lizardi et al. |
| 6,939,365 B1 | 9/2005 | Fogarty et al. |
| 6,946,003 B1 | 9/2005 | Wolowacz et al. |
| 6,949,117 B2 | 9/2005 | Gambale et al. |
| 6,964,685 B2 | 11/2005 | Murray et al. |
| 6,966,916 B2 | 11/2005 | Kumar |
| 6,972,027 B2 | 12/2005 | Fallin et al. |
| 6,984,241 B2 | 1/2006 | Lubbers et al. |
| 6,991,597 B2 | 1/2006 | Gellman et al. |
| 7,008,435 B2 | 3/2006 | Cummins |
| 7,021,316 B2 | 4/2006 | Leiboff |
| 7,025,772 B2 | 4/2006 | Gellman et al. |
| 7,033,379 B2 | 4/2006 | Peterson |
| 7,037,324 B2 | 5/2006 | Martinek |
| 7,048,171 B2 | 5/2006 | Thornton et al. |
| 7,063,711 B1 | 6/2006 | Loshakove et al. |
| 7,083,638 B2 | 8/2006 | Foerster |
| 7,087,064 B1 | 8/2006 | Hyde |
| 7,112,214 B2 | 9/2006 | Peterson et al. |
| 7,118,581 B2 | 10/2006 | Fridén |

(56) References Cited

U.S. PATENT DOCUMENTS

| | | |
|---|---|---|
| 7,144,413 B2 | 12/2006 | Wilford et al. |
| 7,144,414 B2 | 12/2006 | Harvie et al. |
| 7,150,750 B2 | 12/2006 | Damarati |
| 7,153,314 B2 | 12/2006 | Laufer et al. |
| 7,160,314 B2 | 1/2007 | Sgro et al. |
| 7,160,326 B2 | 1/2007 | Ball |
| 7,163,551 B2 | 1/2007 | Anthony et al. |
| 7,163,563 B2 | 1/2007 | Schwartz et al. |
| 7,169,157 B2 | 1/2007 | Kayan |
| 7,189,251 B2 | 3/2007 | Kay |
| 7,201,754 B2 | 4/2007 | Stewart et al. |
| 7,214,232 B2 | 5/2007 | Bowman et al. |
| 7,226,469 B2 | 6/2007 | Benavitz et al. |
| 7,229,452 B2 | 6/2007 | Kayan |
| 7,247,164 B1 | 7/2007 | Ritchart et al. |
| 7,303,577 B1 | 12/2007 | Dean |
| 7,309,337 B2 | 12/2007 | Colleran et al. |
| 7,320,692 B1 | 1/2008 | Bender et al. |
| 7,320,701 B2 | 1/2008 | Haut et al. |
| 7,322,935 B2 | 1/2008 | Palmer et al. |
| 7,326,231 B2 | 2/2008 | Phillips et al. |
| 7,343,920 B2 | 3/2008 | Toby et al. |
| 7,368,124 B2 | 5/2008 | Chun et al. |
| 7,377,934 B2 | 5/2008 | Lin et al. |
| 7,381,213 B2 | 6/2008 | Lizardi |
| 7,390,329 B2 | 6/2008 | Westra et al. |
| 7,399,304 B2 | 7/2008 | Gambale et al. |
| 7,404,824 B1 | 7/2008 | Webler et al. |
| 7,416,554 B2 | 8/2008 | Lam et al. |
| 7,452,368 B2 | 11/2008 | Liberatore et al. |
| 7,460,913 B2 | 12/2008 | Kuzma et al. |
| 7,463,933 B2 | 12/2008 | Wahlstrom et al. |
| 7,465,308 B2 | 12/2008 | Sikora et al. |
| 7,481,832 B1 | 1/2009 | Meridew et al. |
| 7,485,124 B2 | 2/2009 | Kuhns et al. |
| 7,497,854 B2 | 3/2009 | Gill et al. |
| 7,500,972 B2 | 3/2009 | Voegele et al. |
| 7,500,980 B2 | 3/2009 | Gill et al. |
| 7,500,983 B1 | 3/2009 | Kaiser et al. |
| 7,503,474 B2 | 3/2009 | Hillstead et al. |
| 7,506,791 B2 | 3/2009 | Omaits et al. |
| 7,559,941 B2 | 7/2009 | Zannis et al. |
| 7,572,276 B2 | 8/2009 | Lim et al. |
| 7,585,311 B2 | 9/2009 | Green et al. |
| 7,766,208 B2 | 8/2010 | Epperly et al. |
| 7,771,440 B2 | 8/2010 | Ortiz et al. |
| 7,776,057 B2 | 8/2010 | Laufer et al. |
| 7,780,685 B2 | 8/2010 | Hunt et al. |
| 7,785,255 B2 | 8/2010 | Malkani |
| 7,807,192 B2 | 10/2010 | Li et al. |
| 7,819,880 B2 | 10/2010 | Zannis et al. |
| 7,819,888 B2 | 10/2010 | Johanson et al. |
| 7,918,879 B2 | 4/2011 | Yeung et al. |
| 7,931,660 B2 | 4/2011 | Aranyi et al. |
| 8,034,076 B2 | 10/2011 | Criscuolo et al. |
| 8,114,101 B2 | 2/2012 | Criscuolo et al. |
| 8,197,837 B2 | 6/2012 | Jamiolkowski et al. |
| 8,668,718 B2 | 3/2014 | Euteneuer et al. |
| 8,763,878 B2 | 7/2014 | Euteneuer et al. |
| 8,821,536 B2 | 9/2014 | Euteneuer et al. |
| 8,821,537 B2 | 9/2014 | Euteneuer et al. |
| 8,864,780 B2 | 10/2014 | Euteneuer et al. |
| 8,894,669 B2 | 11/2014 | Nering et al. |
| 9,033,201 B2 | 5/2015 | Euteneuer |
| 9,095,337 B2 | 8/2015 | Euteneuer et al. |
| 9,101,460 B2 | 8/2015 | Euteneuer et al. |
| 9,107,661 B2 | 8/2015 | Euteneuer et al. |
| 9,113,977 B2 | 8/2015 | Euteneuer et al. |
| 9,125,650 B2 | 9/2015 | Euteneuer et al. |
| 9,179,961 B2 | 11/2015 | Euteneuer et al. |
| 9,192,013 B1 | 11/2015 | van de Ven et al. |
| 9,198,751 B2 | 12/2015 | Euteneuer et al. |
| 9,204,940 B2 | 12/2015 | Euteneuer et al. |
| 9,247,978 B2 | 2/2016 | Euteneuer et al. |
| 9,271,726 B2 | 3/2016 | Euteneuer |
| 9,314,314 B2 | 4/2016 | Euteneuer et al. |
| 9,314,331 B2 | 4/2016 | Euteneuer et al. |
| 9,370,356 B2 | 6/2016 | Euteneuer et al. |
| 9,393,103 B2 | 7/2016 | Van Kampen et al. |
| 2002/0077687 A1 | 6/2002 | Ahn |
| 2002/0090725 A1 | 7/2002 | Simpson et al. |
| 2002/0123767 A1 | 9/2002 | Prestel |
| 2002/0165559 A1 | 11/2002 | Grant et al. |
| 2002/0169465 A1 | 11/2002 | Bowman et al. |
| 2003/0073979 A1 | 4/2003 | Naimark et al. |
| 2003/0125748 A1 | 7/2003 | Li et al. |
| 2003/0135224 A1 | 7/2003 | Blake, III |
| 2003/0212456 A1 | 11/2003 | Lipchitz et al. |
| 2004/0059416 A1 | 3/2004 | Murray et al. |
| 2004/0092937 A1 | 5/2004 | Criscuolo et al. |
| 2004/0138705 A1 | 7/2004 | Heino et al. |
| 2004/0167519 A1 | 8/2004 | Weiner et al. |
| 2004/0220574 A1 | 11/2004 | Pelo et al. |
| 2005/0015021 A1 | 1/2005 | Shiber |
| 2005/0049618 A1 | 3/2005 | Masuda et al. |
| 2005/0051597 A1 | 3/2005 | Toledano |
| 2005/0059996 A1 | 3/2005 | Bauman et al. |
| 2005/0060033 A1 | 3/2005 | Vacanti et al. |
| 2005/0107807 A1 | 5/2005 | Nakao |
| 2005/0113736 A1 | 5/2005 | Orr et al. |
| 2005/0171569 A1 | 8/2005 | Girard et al. |
| 2005/0187576 A1 | 8/2005 | Whitman et al. |
| 2005/0240222 A1 | 10/2005 | Shipp |
| 2005/0274768 A1 | 12/2005 | Cummins et al. |
| 2006/0074423 A1 | 4/2006 | Alleyne et al. |
| 2006/0178743 A1 | 8/2006 | Carter |
| 2006/0235442 A1 | 10/2006 | Huitema |
| 2006/0293760 A1 | 12/2006 | DeDeyne |
| 2007/0078477 A1 | 4/2007 | Heneveld, Sr. et al. |
| 2007/0083236 A1 | 4/2007 | Sikora |
| 2007/0112361 A1 | 5/2007 | Schonholz et al. |
| 2007/0179531 A1 | 8/2007 | Thornes |
| 2007/0185506 A1 | 8/2007 | Jackson |
| 2007/0190108 A1 | 8/2007 | Datta et al. |
| 2007/0219558 A1 | 9/2007 | Deutsch |
| 2007/0270804 A1 | 11/2007 | Chudik |
| 2007/0288023 A1 | 12/2007 | Pellegrino et al. |
| 2008/0027470 A1 | 1/2008 | Hart et al. |
| 2008/0051888 A1 | 2/2008 | Ratcliffe et al. |
| 2008/0065153 A1 | 3/2008 | Allard et al. |
| 2008/0090936 A1 | 4/2008 | Fujimura et al. |
| 2008/0125869 A1 | 5/2008 | Paz et al. |
| 2008/0135600 A1 | 6/2008 | Hiranuma et al. |
| 2008/0139473 A1 | 6/2008 | Ladner et al. |
| 2008/0173691 A1 | 7/2008 | Mas et al. |
| 2008/0188874 A1 | 8/2008 | Henderson |
| 2008/0188936 A1 | 8/2008 | Ball et al. |
| 2008/0195119 A1 | 8/2008 | Ferree |
| 2008/0200949 A1 | 8/2008 | Hiles et al. |
| 2008/0241213 A1 | 10/2008 | Chun et al. |
| 2008/0272173 A1 | 11/2008 | Coleman et al. |
| 2008/0306408 A1 | 12/2008 | Lo |
| 2008/0312688 A1 | 12/2008 | Nawrocki et al. |
| 2009/0001122 A1 | 1/2009 | Prommersberger et al. |
| 2009/0012521 A1 | 1/2009 | Axelson, Jr. et al. |
| 2009/0030434 A1 | 1/2009 | Paz et al. |
| 2009/0069806 A1 | 3/2009 | De La Mora Levy et al. |
| 2009/0076541 A1 | 3/2009 | Chin et al. |
| 2009/0105535 A1 | 4/2009 | Green et al. |
| 2009/0112085 A1 | 4/2009 | Eby |
| 2009/0134198 A1 | 5/2009 | Knodel et al. |
| 2009/0156986 A1 | 6/2009 | Trenhaile |
| 2009/0156997 A1 | 6/2009 | Trenhaile |
| 2009/0182245 A1 | 7/2009 | Zambelli |
| 2009/0242609 A1 | 10/2009 | Kanner |
| 2010/0145367 A1 | 6/2010 | Ratcliffe |
| 2010/0147922 A1 | 6/2010 | Olson |
| 2010/0163598 A1 | 7/2010 | Belzer |
| 2010/0191332 A1 | 7/2010 | Euteneuer et al. |
| 2010/0211097 A1 | 8/2010 | Hadba et al. |
| 2010/0241227 A1 | 9/2010 | Euteneuer et al. |
| 2010/0249801 A1 | 9/2010 | Sengun et al. |
| 2010/0256675 A1 | 10/2010 | Romans |
| 2010/0274278 A1 | 10/2010 | Fleenor et al. |

(56) References Cited

U.S. PATENT DOCUMENTS

| | | |
|---|---|---|
| 2010/0292715 A1 | 11/2010 | Nering et al. |
| 2010/0292791 A1 | 11/2010 | Lu et al. |
| 2010/0312250 A1 | 12/2010 | Euteneuer et al. |
| 2010/0312275 A1 | 12/2010 | Euteneuer et al. |
| 2010/0327042 A1 | 12/2010 | Amid et al. |
| 2011/0000950 A1 | 1/2011 | Euteneuer et al. |
| 2011/0004221 A1 | 1/2011 | Euteneuer et al. |
| 2011/0011917 A1 | 1/2011 | Loulmet |
| 2011/0034942 A1 | 2/2011 | Levin et al. |
| 2011/0040310 A1 | 2/2011 | Levin et al. |
| 2011/0040311 A1 | 2/2011 | Levin et al. |
| 2011/0066166 A1 | 3/2011 | Levin et al. |
| 2011/0079627 A1 | 4/2011 | Cardinale et al. |
| 2011/0106154 A1 | 5/2011 | DiMatteo et al. |
| 2011/0114700 A1 | 5/2011 | Baxter, III et al. |
| 2011/0224702 A1 | 9/2011 | Van Kampen et al. |
| 2011/0264149 A1 | 10/2011 | Pappalardo et al. |
| 2012/0100200 A1 | 4/2012 | Belcheva et al. |
| 2012/0160893 A1 | 6/2012 | Harris et al. |
| 2012/0193391 A1 | 8/2012 | Michler et al. |
| 2012/0209401 A1 | 8/2012 | Euteneuer et al. |
| 2012/0211543 A1 | 8/2012 | Euteneuer |
| 2012/0248171 A1 | 10/2012 | Bailly et al. |
| 2012/0316608 A1 | 12/2012 | Foley |
| 2013/0153627 A1 | 6/2013 | Euteneuer et al. |
| 2013/0153628 A1 | 6/2013 | Euteneuer |
| 2013/0158554 A1 | 6/2013 | Euteneuer et al. |
| 2013/0158587 A1 | 6/2013 | Euteneuer et al. |
| 2013/0158661 A1 | 6/2013 | Euteneuer et al. |
| 2013/0172920 A1 | 7/2013 | Euteneuer et al. |
| 2013/0172997 A1 | 7/2013 | Euteneuer et al. |
| 2013/0184716 A1 | 7/2013 | Euteneuer et al. |
| 2013/0240598 A1 | 9/2013 | Euteneuer et al. |
| 2013/0245627 A1 | 9/2013 | Euteneuer et al. |
| 2013/0245682 A1 | 9/2013 | Euteneuer et al. |
| 2013/0245683 A1 | 9/2013 | Euteneuer et al. |
| 2013/0245693 A1 | 9/2013 | Blain |
| 2013/0245706 A1 | 9/2013 | Euteneuer et al. |
| 2013/0245707 A1 | 9/2013 | Euteneuer et al. |
| 2013/0245762 A1 | 9/2013 | Van Kampen et al. |
| 2013/0245774 A1 | 9/2013 | Euteneuer et al. |
| 2013/0304115 A1* | 11/2013 | Miyamoto ......... A61B 17/2909 606/205 |
| 2014/0358163 A1 | 4/2014 | Farin et al. |
| 2016/0073491 A1 | 3/2016 | Chen et al. |
| 2016/0120542 A1 | 5/2016 | Westling et al. |

FOREIGN PATENT DOCUMENTS

| | | |
|---|---|---|
| EP | 0142225 A1 | 5/1985 |
| EP | 0298400 A1 | 1/1989 |
| EP | 0390613 A1 | 10/1990 |
| EP | 0543499 A1 | 5/1993 |
| EP | 0548998 A1 | 6/1993 |
| EP | 0557963 A1 | 9/1993 |
| EP | 0589306 A2 | 3/1994 |
| EP | 0908152 A1 | 4/1999 |
| EP | 0589306 B1 | 8/1999 |
| EP | 1491157 A1 | 12/2004 |
| EP | 1559379 A1 | 8/2005 |
| EP | 1491157 B1 | 11/2008 |
| EP | 2030576 A2 | 3/2009 |
| GB | 2154688 A | 9/1985 |
| GB | 2397240 A | 7/2004 |
| JP | 58188442 A | 11/1983 |
| JP | 2005586122 A | 3/2005 |
| JP | 2006515774 A | 6/2006 |
| JP | 2012514191 A | 6/2012 |
| JP | 2012528699 A | 11/2012 |
| WO | 8505025 A1 | 11/1985 |
| WO | 0176456 A2 | 10/2001 |
| WO | 0234140 A2 | 5/2002 |
| WO | 03032815 A2 | 4/2003 |
| WO | 2003105670 A2 | 12/2003 |
| WO | 2004000138 A1 | 12/2003 |
| WO | 2004062508 A1 | 7/2004 |
| WO | 2004093690 A1 | 11/2004 |
| WO | 2005016389 A2 | 2/2005 |
| WO | 2006086679 A1 | 8/2006 |
| WO | 2007014910 A1 | 2/2007 |
| WO | 2007030676 A2 | 3/2007 |
| WO | 2007078978 A2 | 7/2007 |
| WO | 2007082088 A2 | 7/2007 |
| WO | 2008065153 A1 | 6/2008 |
| WO | 2008111073 A2 | 9/2008 |
| WO | 2008111078 A2 | 9/2008 |
| WO | 2008139473 A2 | 11/2008 |
| WO | 2009079211 A1 | 6/2009 |
| WO | 2009143331 A1 | 11/2009 |
| WO | 2010141872 A1 | 12/2010 |
| WO | 2010141907 A1 | 12/2010 |
| WO | 2011095890 A2 | 8/2011 |
| WO | 2011128903 A2 | 10/2011 |
| WO | 2013007764 A2 | 1/2013 |
| WO | 2013119321 A1 | 8/2013 |

OTHER PUBLICATIONS

"Rotator Cuff Tear," Wikipedia, the free encyclopedia, 14 pages, Downloaded on Dec. 6, 2012.

Alexander et al., "Ligament and tendon repair with an absorbable polymer-coated carbon fiber stent," Bulletin of the Hospital for Joint Diseases Orthopaedic Institute, 46(2):155-173, 1986.

Bahler et al., "Trabecular bypass stents decrease intraocular pressure in cultured human anterior segments," Am. J. Ophthalmology, 138(6):988-994, Dec. 2004.

Chamay et al., "Digital contracture deformity after implantation of a silicone prosthesis: Light and electron microscopic study," The Journal of Hand Surgery, 3(3):266-270, May 1978.

D'Ermo et al., "Our results of the operation of ab externo trabeculotomy," Opthalmologica, 168: 347-355, 1971.

France et al., "Biomechanical evaluation of rotator cuff fixation methods," The American Journal of Sports Medicine, 17(2), 1989.

Goodship et al., "An assessment of filamentous carbon fibre for the treatment of tendon injury in the horse," Veterinary Record, 106: 217-221, Mar. 8, 1980.

Hunter et al., "Flexor-tendon reconstruction in severely damaged hands," The Journal of Bone and Joint Surgery (American Volume), 53-A(5): 329-358, Jul. 1971.

Johnstone et al., "Microsurgery of Schlemm's canal and the human aqueous outflow system," Am. J. Ophthalmology, 76(6): 906-917, Dec. 1973.

Kowalsky et al., "Evaluation of suture abrasion against rotator cuff tendon and proximal humerus bone," Arthroscopy: The Journal of Arthroscopic and Related Surgery, 24(3):329-334, Mar. 2008.

Lee et al., "Aqueous-venous and intraocular pressure. Preliminary report of animal studies," Investigative Ophthalmology, 5(1): 59-64, Feb. 1966.

Maepea et al., "The pressures in the episcleral veins, Schlemm's canal and the trabecular meshwork in monkeys: Effects of changes in intraocular pressure," Exp. Eye Res., 49:645-663, 1989.

Nicolle et al., "A silastic tendon prosthesis as an adjunct to flexor tendon grafting: An experimental and clinical evaluation," British Journal of Plastic Surgery, 22(3-4):224-236, 1969.

Rubin et al., "The use of acellular biologic tissue patches in foot and ankle surgery," Clinics in Podiatric Medicine and Surgery, 22:533-552, 2005.

Schultz, "Canaloplasty procedure shows promise for open-angle glaucoma in European study," Ocular Surgery News, 34-35, Mar. 1, 2007.

Spiegel et al., "Schlemm's canal implant: a new method to lower intraocular pressure in patients with POAG," Opthalmic Surgery and Lasers, 30(6):492-494, Jun. 1999.

Stenson et al., "Arthroscopic treatment of partial rotator cuff tears," Operative Techniques in Sports Medicine, 12 (2):135-148, Apr. 2004.

(56) References Cited

OTHER PUBLICATIONS

Valdez et al., "Repair of digital flexor tendon lacerations in the horse, using carbon fiber implants," JAYMA, 177(5): 427-435, Sep. 1, 1980.

* cited by examiner

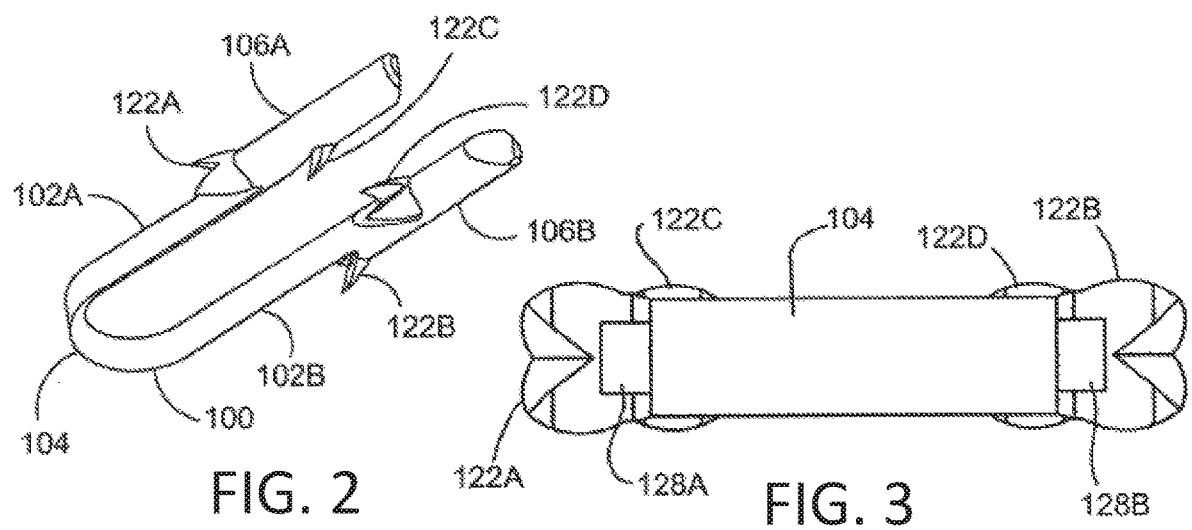
FIG. 2
FIG. 3
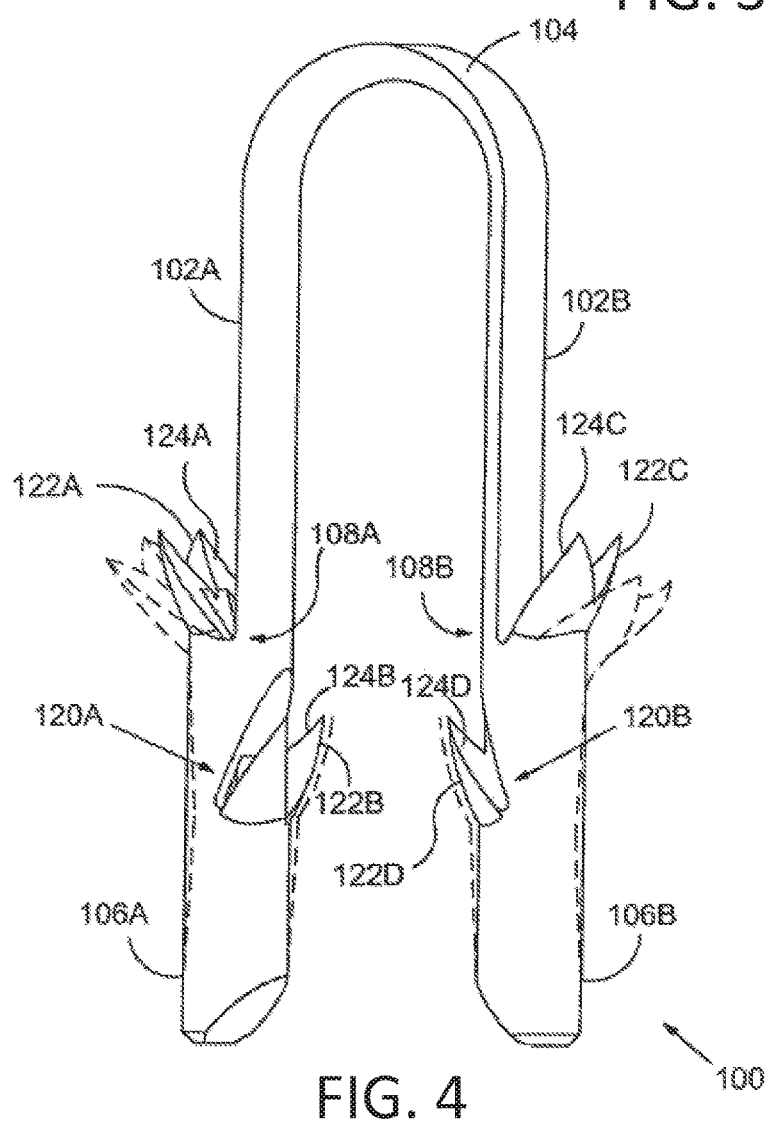
FIG. 4

MEDICAL IMPLANT DELIVERY SYSTEM AND RELATED METHODS

CROSS REFERENCE TO RELATED APPLICATIONS

This application claims the benefit of U.S. Provisional Patent Application Ser. No. 62/074,982 filed on Nov. 4, 2014, the disclosure of which is incorporated herein by reference. This application is also related to U.S. Provisional Patent Application Ser. No. 62/075,026 filed on Nov. 4, 2014, the disclosure of which is incorporated herein by reference.

TECHNICAL FIELD

The present disclosure pertains generally, but not by way of limitation, to medical devices, and methods for using medical devices. More particularly, the present disclosure pertains to devices for introducing and positioning implants within patients, and methods for using such devices.

BACKGROUND

With its complexity, range of motion and extensive use, a common soft tissue injury is damage to the rotator cuff or rotator cuff tendons. Damage to the rotator cuff is a potentially serious medical condition that may occur during hyperextension, from an acute traumatic tear or from overuse of the joint. Adequate procedures do not exist for repairing a partial thickness tear of less than 50% in the supraspinatus tendon. Current procedures attempt to alleviate impingement or make room for movement of the tendon to prevent further damage and relieve discomfort but do not repair or strengthen the tendon. Use of the still damaged tendon can lead to further damage or injury. There is an ongoing need to deliver and adequately position medical implants during an arthroscopic procedure in order to treat injuries to the rotator cuff, rotator cuff tendons, or other soft tissue or tendon injuries throughout a body.

SUMMARY OF THE DISCLOSURE

The disclosure describes various medical devices and methods for using medical devices to assist in delivering and positioning implants within a body. In a first example, a fastener delivery tool comprises a sheath assembly having at least one position retention member proximate a distal end of the sheath assembly, and a handle assembly coupled to a proximal end of the sheath assembly, the handle assembly comprising a housing, a trigger handle, and an insert connector, wherein an external force applied to the trigger handle in a proximal direction causes displacement of the trigger handle relative to a rest position, wherein displacement of the trigger handle from the rest position within a first displacement range imparts a first amount of force on the insert connector relative to the applied external force and displacement of the trigger handle from the rest position within a second displacement range imparts a second amount of force on the insert connector relative to the applied external force, and wherein the first amount of force is greater than the second amount of force.

Alternatively or additionally, in another example, the fastener delivery further comprises a cam follower connected to the insert connector, and wherein the trigger handle imparts force on the insert connector through the cam follower when the trigger handle is displaced from the rest position.

Alternatively or additionally, in another example, the cam follower comprises a flat portion and a protrusion.

Alternatively or additionally, in another example, within the first displacement range, the cam follower protrusion contacts the trigger handle.

Alternatively or additionally, in another example, within the second displacement range, the cam follower flat portion contacts the trigger handle.

Alternatively or additionally, in another example, the first amount of force is between two times and six times the applied external force.

Alternatively or additionally, in another example, the first amount of force is four times the applied external force.

Alternatively or additionally, in another example, the second amount of force is between one and four times the applied external force.

Alternatively or additionally, in another example, the first displacement range is greater than the second displacement range.

Alternatively or additionally, in another example, the fastener delivery tool further comprises a spring connected to the housing and the trigger handle, wherein the spring biases the trigger handle to the rest position.

In another example, a fastener delivery tool comprises a sheath assembly comprising a lumen and configured to receive one or more inserts at least partially within the lumen, and a handle assembly connected to the sheath assembly, the handle assembly comprising a trigger handle, wherein, when an insert is received within the sheath assembly, movement of the trigger handle relative to a rest position within a first movement range imparts a first amount of force on the received insert, and wherein movement of the trigger handle relative to the rest position within second movement range imparts a second amount of force on the received insert, wherein the first amount of force is greater than the second amount of force.

Alternatively or additionally, in another example, the first movement range and the second movement range do not overlap.

Alternatively or additionally, in another example, the first movement range is greater than the second movement range.

Alternatively or additionally, in another example, the first amount of force is between two times and five times the second amount of force.

Alternatively or additionally, in another example, the first amount of force is three times the second amount of force.

In yet another example, a method for deploying a fastener into bone comprises positioning a position retention sleeve proximate the bone, the position retention sleeve having one or more position retention members proximate a distal end of the position retention sleeve, and wherein the position retention sleeve is coupled to a handle assembly, the handle assembly comprising a trigger handle, inserting a pilot hole forming assembly into a lumen of the position retention sleeve, the pilot hole forming assembly having one or more pilot hole forming members proximate a distal end of the pilot hole forming assembly, driving the one or more pilot hole forming members and the one or more position retention members into the bone, applying force to the trigger handle to remove the pilot hole forming assembly from the lumen of the position retention sleeve while retaining the one or more position retention members in the bone, wherein the trigger handle imparts the applied force to the pilot hole forming assembly with a first force multiplier in a first stage and with a second force multiplier in a second stage, wherein the first force multiplier is greater than the second force multiplier, inserting a staple delivery device into the lumen of the position retention of sleeve, and deploying a staple into the bone.

Alternatively or additionally, in another example, the first stage comprises a first range of displacements of the trigger handle from a rest position, wherein the second stage comprises a second range of displacements of the trigger handle from the rest position, and wherein the first range of displacements is greater than the second range of displacements.

Alternatively or additionally, in another example, when the pilot hole forming assembly is received within the position retention sleeve, the one or more pilot hole forming members extend distal of the one or more position retention members a first amount, wherein after the one or more pilot hole forming members have been driven into the bone, the one or more pilot hole forming members extend distal of the one or more position retention members a second amount, and wherein the second amount is greater than the first amount.

Alternatively or additionally, in another example, the first amount is between 0.05 inches and 0.35 inches.

Alternatively or additionally, in another example, the second amount is between 0.40 inches and 0.65 inches.

The above summary of some examples is not intended to describe each disclosed example device, component, or method or every implementation of the present disclosure. The Brief Description of the Drawings, and Detailed Description, which follow, more particularly exemplify these examples, but are also intended as exemplary and not limiting.

BRIEF DESCRIPTION OF THE DRAWINGS

FIG. 2 is a an alternative perspective view of the tissue fastener or staple of FIG. 1 illustrating other features in accordance with the present disclosure;

FIG. 3 is a top plan view of the tissue fastener or staple of FIG. 1 illustrating the laterally extending legs having lumens for receiving the stakes of a delivery device of the present disclosure;

FIG. 4 is a front plan view of the tissue fastener or staple of FIG. 1 illustrating in phantom flexing of the barbs and legs of the staple in response to grasping of tissue in one example of the present disclosure;

DETAILED DESCRIPTION

Figure 1:
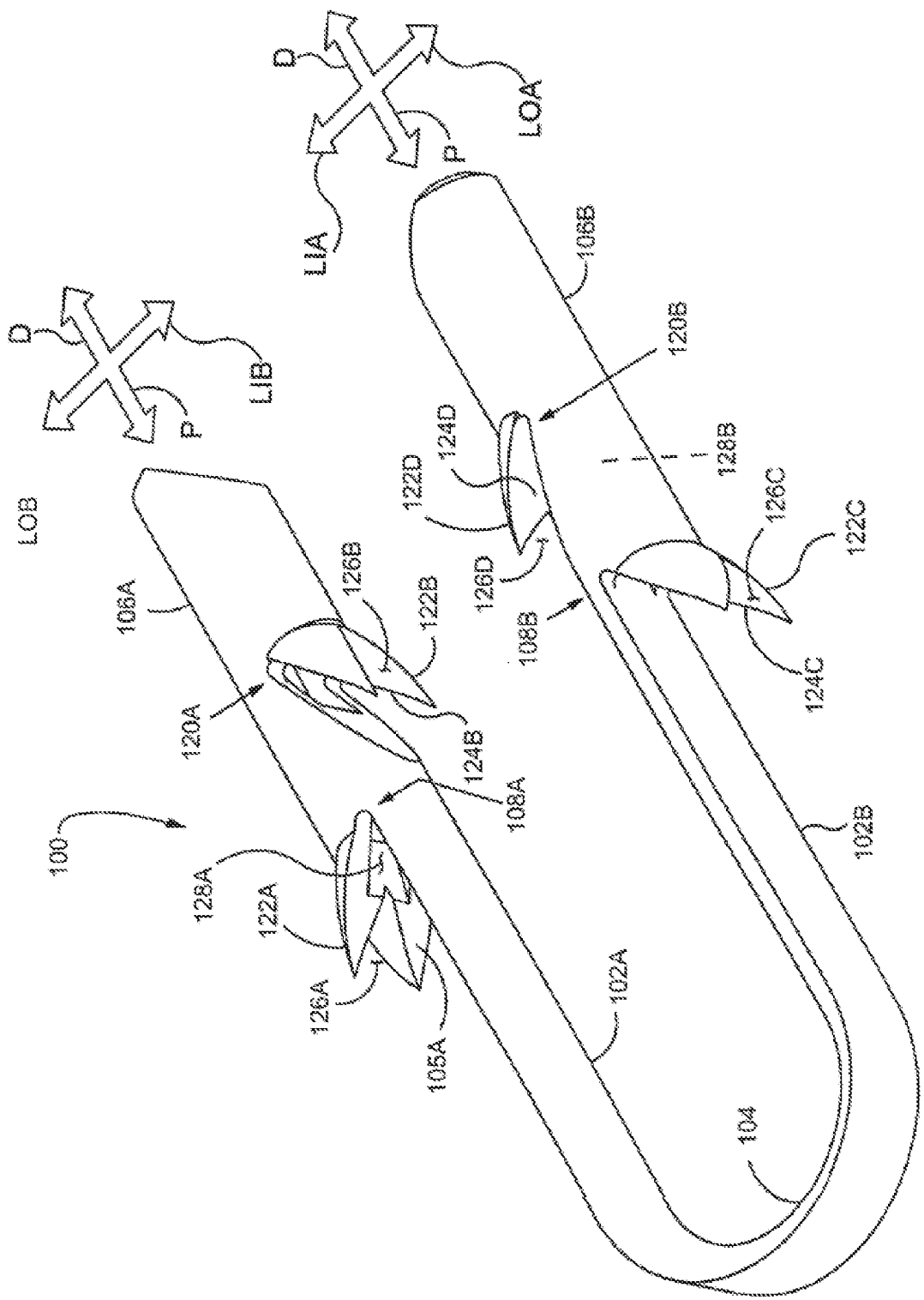
FIG. 1 is a perspective view illustrating an exemplary tissue fastener or staple in accordance with the present disclosure.

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate examples of the claimed invention.

Definitions of certain terms are provided below and shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same or substantially the same function or result). In many instances, the terms "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

It is noted that references in the specification to "an embodiment", "some embodiments", "other embodiments", "an example", "some examples", "other examples", etc., indicate that the embodiment(s) and/or example(s) described may include a particular feature, structure, or characteristic, but every embodiment may not necessarily include the particular feature, structure, or characteristic. Moreover, such phrases are not necessarily referring to the same embodiment and/or example. Further, when a particular feature, structure, or characteristic is described in connection with an embodiment and/or example, it would be within the knowledge of one skilled in the art to affect such feature, structure, or characteristic in connection with other embodiments and/or examples, whether or not explicitly described, unless clearly stated to the contrary. That is, the various individual features described below, even if not explicitly shown in a particular combination, are nevertheless contemplated as being combinable or able to be arranged with each other to form other additional embodiments and/or examples or to complement and/or enrich the described embodiment(s) and/or example(s), as would be understood by one of ordinary skill in the art.

FIG. 1 is a perspective view illustrating an exemplary staple 100 in accordance with the present disclosure. Although the various parts of exemplary staple 100 are depicted in relative proportion to other parts of staple 100, other configurations in size and orientation of the various parts are also contemplated in other examples. A number of reference directions are illustrated using arrows in FIG. 1 to assist in understanding the details of staple 100. The illustrated directions include: proximal direction P, distal direction D, first laterally outward direction LOA, second laterally outward direction LOB, first laterally inward direction LIA, and second laterally inward direction LIB.

In some examples, staple 100 comprises first arm 102A, second arm 102B, and bridge 104. Bridge 104 may abut, or extend from or adjacent to, the proximal end of first arm 102A to the proximal end of second arm 102B. First arm 102A may include first trunk 106A, with first trunk 106A generally having a greater width than the rest of first arm 102A as depicted in FIG. 1. In some examples, first arm 102A may also include non-trunk portion 105A. The length of first trunk 106A relative to the overall length of first arm 102A can vary in different examples. For instance, first trunk 106A can extend for the entire length of first arm 102A such that bridge 104 abuts with or is adjacent to first trunk 106A. In other examples, first arm 102A may not include first trunk 106A. That is, first arm 102A may not have a portion with a greater width than the rest of first arm 102A. In such examples, first arm 102A may still have non-trunk portion 105A.

Similarly, second arm 102B may include second trunk 106B, with second trunk 106B generally having a greater width than the rest of second arm 102B. Additionally, second trunk 106B may extend for at least a portion of second arm 102B. A distal portion of second arm 102B may abut the proximal end of second trunk 106B and second arm 102B may further include non-trunk portion 105B. As with first trunk 106A, second trunk 106B may extend along second arm 102B for varying lengths. Additionally, in some examples, second arm 102B may not have a portion with a greater width than the rest of second arm 102B. In FIG. 1, first trunk 106A and second trunk 106B are shown extending distally from a proximal portion of first arm 102A and second arm 102B, respectively.

In the example of FIG. 1, first trunk 106A has a lateral extent, or cross sectional area, that is larger than a lateral extent of the non-trunk portion 105A of first arm 102A and bridge 104. Staple 100 may include a first change in lateral stiffness 108A disposed where the distal end of non-trunk portion 105A of first arm 102A abuts first trunk 106A. As depicted, the change in stiffness is abrupt, but can be gradual in alternative examples—such as through a gradual change in lateral extent between first trunk 106A and non-trunk portion 105A. In an example where first trunk 106A extends for the full length of the first arm 102A, the change in stiffness may occur where first trunk 106A abuts bridge 104. With reference to the example of FIG. 1, it will be appreciated that first trunk 106A is mounted eccentrically to first arm 102A and second trunk 106B is mounted eccentrically to second arm 102B. As with first trunk 106A, second trunk 106B has a lateral extent, or cross sectional area that is larger than a lateral extent of second arm 102B or bridge 104. Staple 100 may include a second change in lateral stiffness 108B where the distal end of second arm 102B abuts second trunk 106A. Similarly to first arm 102A, in some examples the change in stiffness may be abrupt or gradual. If second trunk 106B extends for the entire length of second arm 102B, the change in stiffness may occur at the abutment with bridge 104. In additional examples where there may be no change in lateral extent between first and second trunks 106A, 106B and first and second arms 102A, 102B, a change in stiffness may be accomplished by the use of different materials for first and second trunks 106A, 106B and first and second arms 102A, 102B.

Some examples of staple 100 may include at least a first projection 122A, 122C and a second projection 122B, 122D, on each of first trunk 106A and second trunk 106B, respectively. First projection 122A, 122C on each trunk 106A, 106B may further include first proximal surface 124A, 124C extending away from each trunk in a first direction, such as out and away from each opposite trunk 106A, 106B. The first direction may be a direction such that first proximal surface 124A, 124C will engage with tissue or bone after the trunk is inserted therein and by natural movement of the tissue or bone. In some examples, a pullout force may be applied to bridge 104 to further engage first proximal surface 124A, 124C with bone or tissue. The natural movement of the bone or tissue or the pullout force creates a first moment centered on the area of reduced stiffness adjacent each trunk, tending to rotate each trunk thereabout. The rotation of each trunk may further provide a greater holding force of staple 100 in bone or tissue. Second projection 122B, 122D may include second proximal surface 124B, 124D extending away from each trunk in a second direction, different from the first direction, such as inward, toward the opposite trunk. For example, the second direction may be selected such that second proximal surfaces 124B, 124D will engage tissue or bone after each trunk is inserted therein and by natural movement of the tissue or bone. In some examples, a pullout force may be applied to bridge 104. A slit or area of reduced cross section in the trunk adjacent the second projections provide an area of weakness so that a second moment is applied to the trunk in response to natural movement of the tissue or bone and/or to a pullout force on bridge 104. This moment causes rotation of the trunk about the area of weakness and increases the holding force of staple 100.

As illustrated in the example of staple 100 in FIG. 1, first trunk 106A includes a first projection 122A disposed at an outer side of trunk 106A and a second projection 122B disposed at an inner side of the trunk. First projection 122A includes a first proximal surface 124A extending away from first trunk 106A in a first direction. With reference to FIG. 1, it will be appreciated that the first direction has an outward lateral component and a proximal component so that first proximal surface 124A extends outwardly and proximally away from first trunk 106A. For example, the first direction may be selected such that first proximal surface 124A will engage tissue or bone proximate the outer side of first trunk 106A after being inserted therein so that a first moment is applied to the trunk in response to natural movement of the tissue or bone and/or to a pullout force on bridge 104. The moment centers on the arm portion of lesser stiffness adjacent the first projection.

In the example of FIG. 1, first trunk 106A includes a first localized area of weakness 120A disposed proximate second projection 122B. Second projection 122B includes a second proximal surface 124B extending away from first trunk 106A in a second direction. The second direction is selected such that second proximal surface 124A will engage tissue or bone proximate the inner side of first trunk 106A when inserted therein so that a second moment is applied to the trunk in response to natural movement of the tissue or bone and/or a pullout force on bridge 104. The moment centers around the area of weakness 120A. The second moment has a direction that is generally opposite a direction of the first moment. It will be appreciated that the second direction has an inward lateral component and a proximal component so that second proximal surface 124B extends inwardly and proximally away from first trunk 106A. In other examples, first arm 102A may not include second projection 122B. In such examples, only a first moment may be applied to first trunk 106A in response to natural movement of the tissue or bone and/or a pullout force on bridge 104.

Second trunk 106B includes a third projection 122C disposed at an outer side of second trunk 106B and a fourth projection 122D disposed at an inner side of the trunk. In the example of FIG. 1, third projection 122C includes a third proximal surface 124C extending away from second trunk 106B in a third direction. With reference to FIG. 1, it will be appreciated that the third direction has an outward lateral component and a proximal component so that third proximal surface 124C extends outwardly and proximally away from second trunk 106B. The third direction is selected such that third proximal surface 124C will engage tissue or bone proximate the outer side of second trunk 106B when inserted therein so that a third moment is applied to the trunk in response to natural movement of the tissue or bone and/or a pullout force on bridge 104.

In the example of FIG. 1, second trunk 106B includes a second localized area of weakness 120B disposed proximate fourth projection 122D. Fourth projection 122D includes a fourth proximal surface 124D extending away from second trunk 106B in a fourth direction. In the example of FIG. 1, the fourth direction is selected such that second proximal surface 124A will engage tissue or bone proximate the inner side of second trunk 106B when inserted therein so that a fourth moment is applied to the trunk in response to natural movement of the tissue or bone and/or a pullout force on bridge 104. The fourth moment has a direction that is generally opposite a direction of the third moment. It will be appreciated that the fourth direction has an inward lateral component and a proximal component so that fourth proximal surface 124D extends inwardly and proximally away from second trunk 106B. In other examples, second arm 102B may not include second projection 122D. In such examples, only a first moment may be applied to second trunk 106B in in response to natural movement of the tissue or bone and/or a pullout force on bridge 104.

As depicted in FIG. 1, the staple 100 includes proximal projections that extend away from or outward from the bridge 104, while the distal projections extend inward or toward the center of the bridge 104. This creates generally opposing forces in response to tension on the bridge which, in combination with areas of weakness or reduced lateral extent, substantially increases the holding force of the staple in bone as the different portions of the trunks tend to rotate in opposite directions and apply force to an opposing wall in the hole in bone in which the staple is positioned. It is however, understood that other configurations of the projections are possible. In some examples, only two projections are included and they extend in different directions to cause different force responses as tension is applied to the bridge. Additional examples may include varying numbers of projections which produce one or more moments in each of arms 102A, 102B.

In some examples, each projection of staple 100 may be clefted to form a plurality of points for greater retention in tissue. In the example of FIG. 1, first projection 122A of first trunk 106A defines a first notch 126A that divides first projection 122A into a first sub-projection and a second sub-projection. Second projection 122B of second trunk 106B defines a second notch 126B. In the example of FIG. 1, second notch 126B divides second projection 122B into a first sub-projection and a second sub-projection. Third projection 122C of second trunk 106B defines a third notch 126C that divides third projection 122C into a first sub-projection and a second sub-projection. Fourth projection 122D of second trunk 106B defines a fourth notch 126D that divides fourth projection 122D into a first sub-projection and a second sub-projection.

With continued reference to FIG. 1 and further reference to FIGS. 2 and 3, first trunk 106A defines a first cavity 128A and second trunk 106B defines a second cavity 128B. In the examples of FIGS. 1, 2 and 3, first cavity 128A extends into first trunk 106A and second cavity 128B extends into second trunk 106B. The cavity is sized to cooperate with a staple delivery device for holding and inserting the staple into tissue or bone, as later described in detail herein. In summary, the staple delivery device includes longitudinally extending stakes that fit within the cavities 128A, 128B to hold the staple 100 and push it into position in the tissue as the stake abuts a portion of its respective trunk. In some examples the cavity may extend through a portion of the length of each trunk, as best depicted in FIG. 2 which indicates the distal end of the staple 100 is closed. Alternatively, first cavity 128A and second cavity 128B may extend through the entire length of each trunk 106A, 106B or other portions of staple 100 in some examples. As illustrated by the top view of the staple 100 in FIG. 3, first cavity 128A and second cavity 128B each have a generally rectangular or square cross-sectional shape to cooperate with a similarly shaped cross section on a staple delivery device. However, that first cavity 128A and second cavity 128B may have various cross-sectional shapes to cooperate with alternative staple delivery device designs without deviating from the spirit and scope of the present disclosure.

FIG. 4 is an alternative perspective view of example staple 100 depicted in FIG. 1. In particular, FIG. 4 illustrates in phantom the flexing and bending of the trunks 106A and 106B after implant in response to natural movement of the tissue or bone and/or to tension applied to the bridge.

The combination of projections, areas of weakness and changes in lateral extent described with respect to FIGS. 1, 2, and 3 provide desired flexing, bending and rotating of the trunk in response to natural movement of the tissue or bone and/or to pull out forces on bridge 104. Together the various components of staple 100 act as tissue retention members. An exemplary deflected shape is shown with dashed lines in FIG. 4. Forces applied to staple 100 in response to natural movement of the tissue or bone and/or pullout forces applied to bridge 104 may urge staple 100 to assume the deflected shape shown in FIG. 4. In some additional examples, distally directed forces may be applied on staple 100 using, for example, the staple delivery system shown later and described herein. In some applications, the staple delivery tool may be used to urge first projection 122A and third projection 122C into orientations which lock staple 100 into a target tissue. For example, first projection 122A and third projection 122C may be rotated so that these projections engage the target tissue. When this is the case, tension extending through bridge 104 of staple 100 may keep first projection 122A and third projection 122C in the rotated position. Also when this is the case, the projections may inhibit staple pullout. Further, rotation of any projection causes a rotational force and imparts, within limits defined by the hole in the bone, some rotation to an adjacent portion of the trunk which contacts or engages the wall of the hole in the bone. Increased pullout forces, such as by natural movement of the tissue or bone and/or pullout forces applied to bridge 104, may result in increasing holding force with this design.

Figure 5:
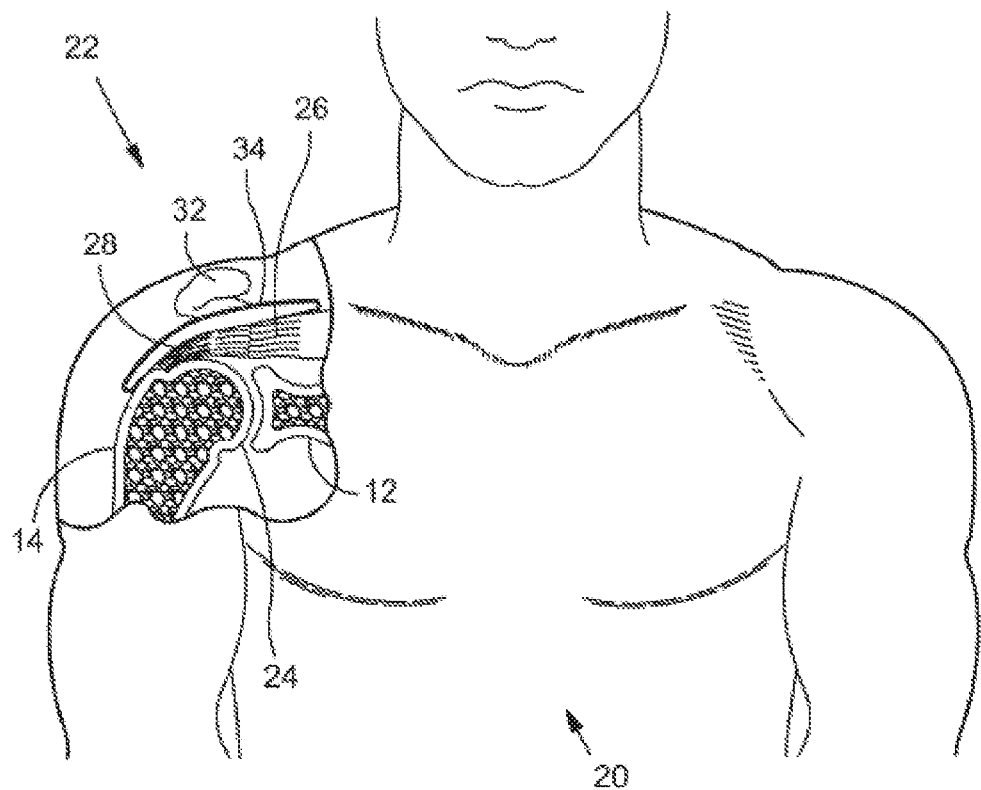
FIG. 5 is a stylized anterior view of a shoulder including a humerus and a scapula.

Next referring to FIG. 5, an exemplary use or application of the staples of the present disclosure is described. FIG. 5 is a stylized anterior view of a patient 20. For purposes of illustration, a shoulder 22 of patient 20 is shown in cross-section in FIG. 5. Shoulder 22 includes a humerus 14 and a scapula 12. In FIG. 5, a head 24 of humerus 14 can be seen mating with a glenoid fossa of scapula 12 at a glenohumeral joint. With reference to FIG. 5, it will be appreciated that the glenoid fossa comprises a shallow depression in scapula 12. The movement of humerus 14 relative to scapula 12 is controlled by a number of muscles including: the deltoid, the supraspinatus, the infraspinatus, the subscapularis, and the teres minor. For purposes of illustration, only the supraspinatus 26 is shown in FIG. 5.

With reference to FIG. 5, a distal tendon 28 of the supraspinatus 26 meets humerus 14 at an insertion point. Scapula 12 of shoulder 22 includes an acromium 32. In FIG. 5, a subacromial bursa 34 is shown extending between acromium 32 of scapula 12 and head 24 of humerus 14. Subacromial bursa 34 is shown overlaying supraspinatus 26 as well as supraspinatus tendon 28 and a portion of humerus 14. Subacromial bursa 34 is one of the hundreds of bursae found the human body. Each bursa comprises a fluid filled sac. The presence of these bursae in the body reduces friction between bodily tissues.

The exemplary staples or fasteners described herein may be used to affix tendon repair implants to various target tissues. The shoulder depicted in FIG. 5 is one example where a tendon repair implant may be affixed to one or more bones associated with an articulating joint, such as the glenohumeral joint. Additionally, the tendon repair implant may be affixed to one or more tendons to be treated. The tendons to be treated may be torn, partially torn, have internal micro-tears, be untorn, and/or be thinned due to age, injury or overuse. The methods and apparatus of the present disclosure and related devices may provide beneficial therapeutic effect on a patient experiencing joint pain believed to be caused by partial thickness tears and/or internal micro-tears. By applying a tendon-repair implant early before a full tear or other injury develops, the implant may cause the tendon to thicken and/or at least partially repair itself, thereby avoiding more extensive joint damage, pain, and the need for more extensive joint repair surgery.

Figure 6:
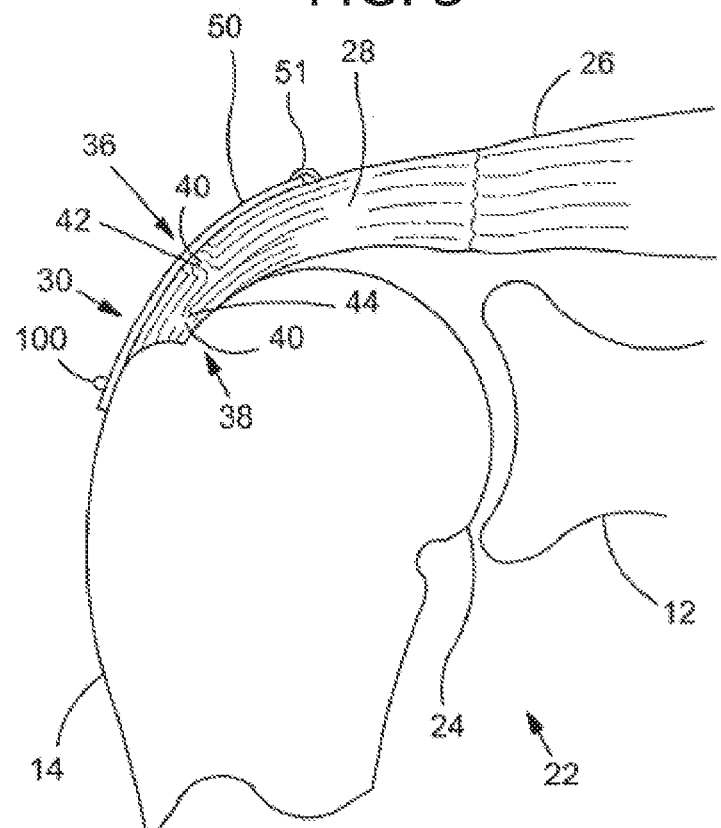
FIG. 6 is a stylized anterior view of a shoulder depicting the head of the humerus shown mating with the glenoid fossa of the scapula at a glenohumeral joint and a sheet-like material is affixed to the tendon.

FIG. 6 is a stylized anterior view of a shoulder 22 including a humerus 14 and a scapula 12. In FIG. 6, a head 24 of humerus 14 is shown mating with a glenoid fossa of scapula 12 at a glenohumeral joint. A supraspinatus 26 is also shown in FIG. 6. This muscle, along with others, controls the movement of humerus 14 relative to scapula 12. A distal tendon 28 of supraspinatus 26 meets humerus 14 at an insertion point 30.

As depicted in FIG. 6, distal tendon 28 includes a first damaged portion 36. A number of loose tendon fibers 40 in first damaged portion 36 are visible in FIG. 6. First damaged portion 36 includes a first tear 42 extending partially through distal tendon 28. First tear 42 may therefore be referred to as a partial thickness tear. With reference to FIG. 6, first tear 42 begins on the side of distal tendon 28 facing the subacromial bursa (shown in the previous Figure) and ends midway through distal tendon 28. Accordingly, first tear 42 may be referred to as a bursal side tear.

With reference to FIG. 6, distal tendon 28 includes a second damaged portion 38 located near insertion point 30. As illustrated, second damaged portion 38 of distal tendon 28 has become frayed and a number of loose tendon fibers 40 are visible. Second damaged portion 38 of distal tendon 28 includes second tear 44. Second tear 44 begins on the side of distal tendon 28 facing the center of the humeral head 24. Accordingly, second damaged portion 38 may be referred to as an articular side tear.

FIG. 6 illustrates sheet-like implant 50 has been placed over the bursal side of distal tendon 28. Sheet-like implant 50 is affixed to distal tendon 28 by a plurality of tendon staples 51. Sheet-like implant 50 is affixed to humerus 14 by one or more bone staples 100 in accordance with designs of staples disclosed herein. Sheet-like implant 50 extends over insertion point 30, first tear 42 and second tear 44. Some methods in accordance with this disclosure may include placing a tendon repair implant on the bursal side of a tendon regardless of whether the tears being treated are on the bursal side, articular side or within the tendon. In some cases the exact location and nature of the tears being treated may be unknown. A tendon repair implant may be applied to the bursal side of a tendon to treat shoulder pain that is most likely caused by one or more partial thickness tears in the tendon.

Figure 7:
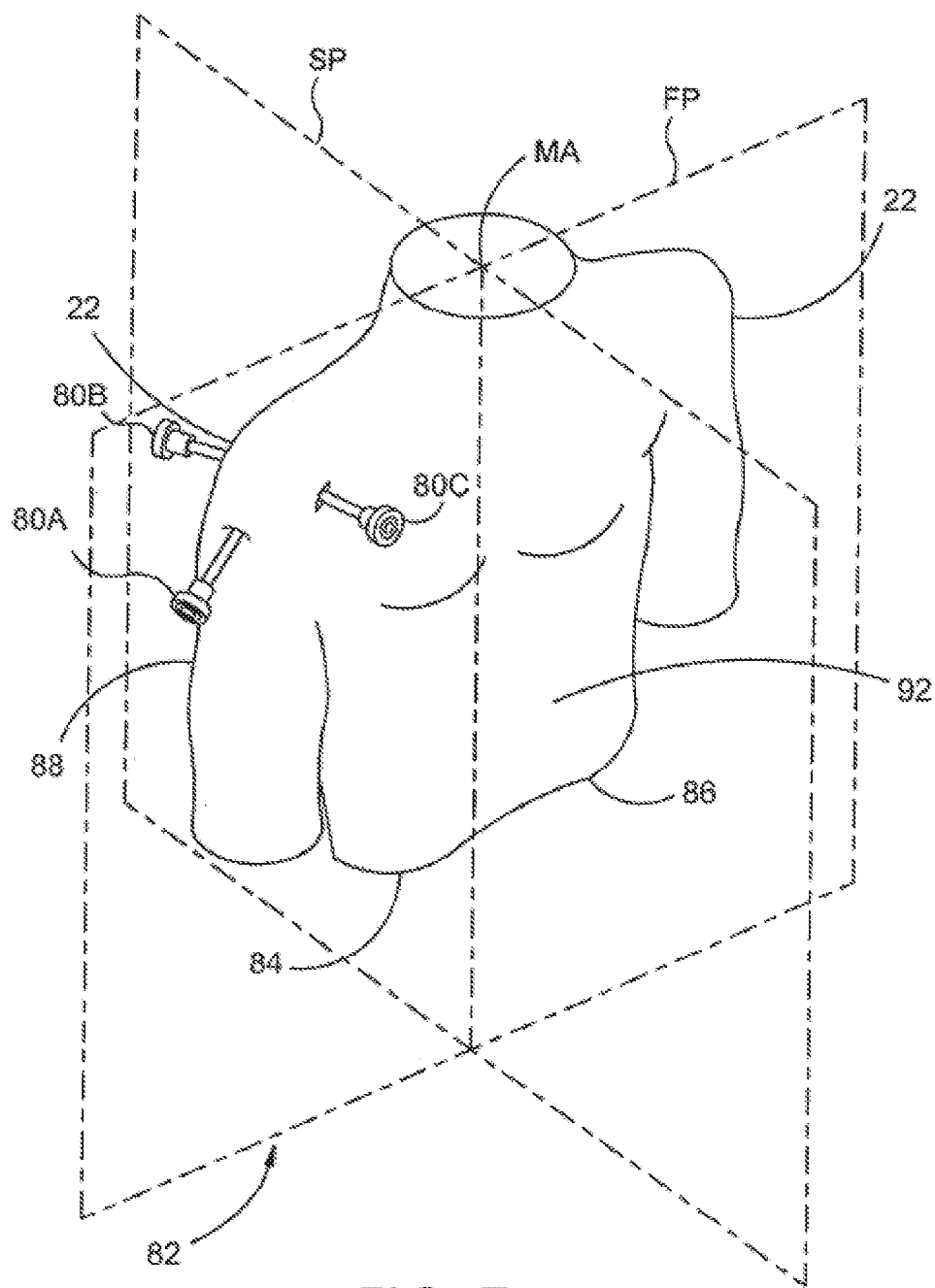
FIG. 7 is a stylized perspective view showing a portion of the body of a human patient divided into quadrants by planes for descriptive purposes herein.

FIG. 7 is a stylized perspective view showing a portion of the body 82 of a human patient 20. Body 82 includes a shoulder 22. In the example of FIG. 7, a plurality of cannulas are positioned to access a treatment site within shoulder 22. In some cases, shoulder 22 may be inflated by pumping a continuous flow of saline through shoulder 22 to create a cavity proximate the treatment site. The cannulas shown in FIG. 7 include a first cannula 80A, a second cannula 80B and a third cannula 80C.

In FIG. 7, a sagital plane SP and a frontal plane FP are shown intersecting body 82. Sagital plane SP and frontal plane FP intersect one another at a medial axis MA of body 82.

With reference to FIG. 7, sagital plane SP bisects body 82 into a right side 84 and a left side 86. Also with reference to FIG. 7, frontal plane FP divides body 82 into an anterior portion 92 and a posterior portion 88. Sagital plane SP and a frontal plane FP are generally perpendicular to one another. These planes and portions are used to describe the procedures used in various examples.

First cannula 80A is accessing a treatment site within shoulder 22 using a lateral approach in which first cannula 80A pierces the outer surface of right side 84 of body 82. The term lateral approach could also be used to describe situations in which an instrument pierces the outer surface of left side 86 of body 82. Second cannula 80B is accessing a treatment site within shoulder 22 using a posterior approach in which second cannula 80B pierces the outer surface of posterior portion 88 of body 82. Third cannula 80C is accessing a treatment site within shoulder 22 using an anterior approach in which third cannula 80C pierces the outer surface of anterior portion 92 of body 82.

Figure 8:
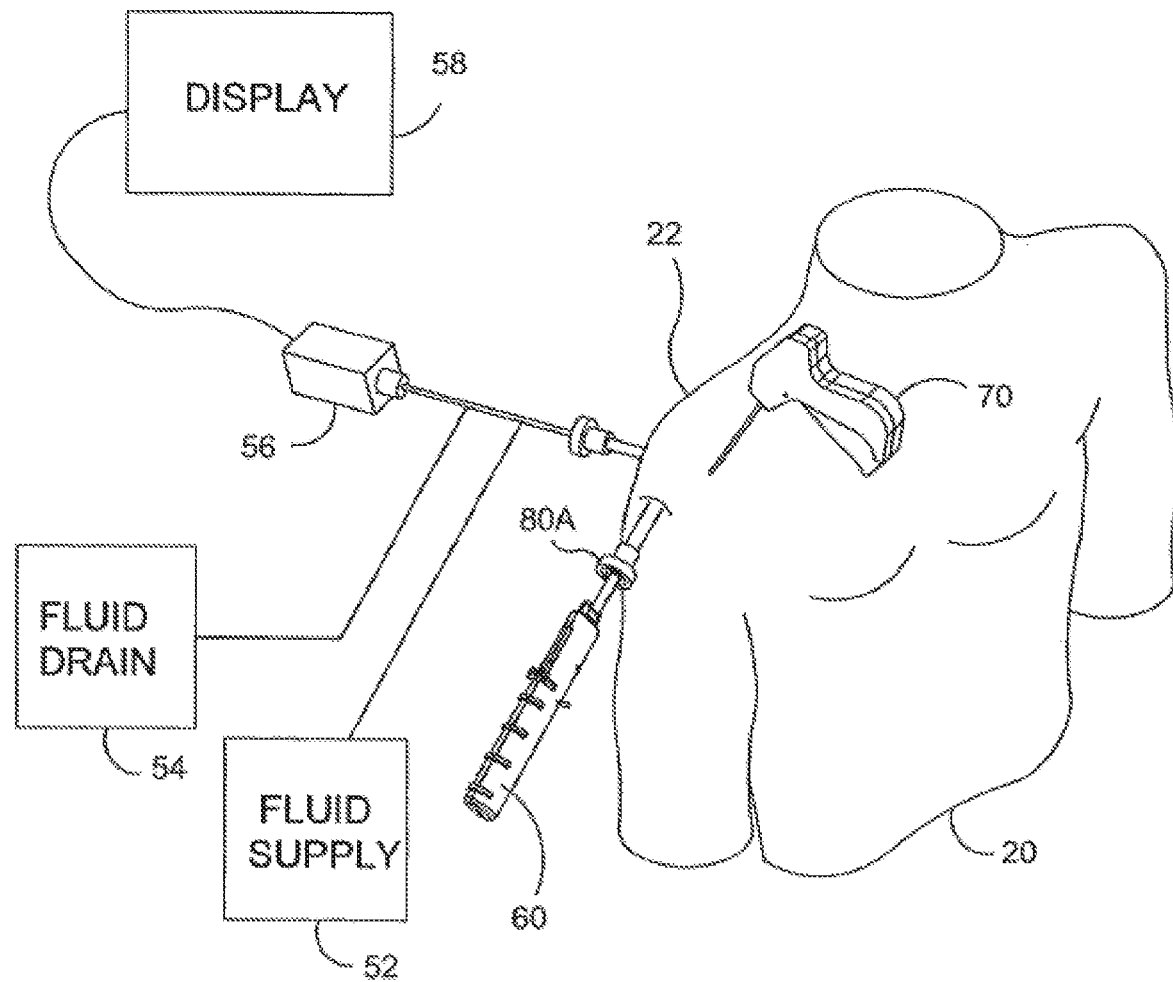
FIG. 8 is a stylized perspective view illustrating an exemplary procedure for arthroscopic treatment of a shoulder of a patient in accordance with one example of the present disclosure.

FIG. 8 is a stylized perspective view illustrating an exemplary procedure for treating a shoulder 22 of a patient 20. The procedure illustrated in FIG. 8 may include, for example, fixing tendon repair implants to one or more tendons of shoulder 22. The tendons treated may be torn, partially torn, have internal micro-tears, be untorn, and/or be thinned due to age, injury or overuse.

Shoulder 22 of FIG. 8 has been inflated to create a cavity therein. A fluid supply 52 is pumping a continuous flow of saline into the cavity. This flow of saline exits the cavity via a fluid drain 54. A camera 56 provides images from inside the cavity. The images provided by camera 56 may be viewed on a display 58.

Camera 56 may be used to visually inspect the tendons of shoulder 22 for damage. A tendon repair implant in accordance with this disclosure may be affixed to a bursal surface of the tendon regardless of whether there are visible signs of tendon damage.

An implant delivery system 60 can be seen extending from shoulder 22 in FIG. 8. Implant delivery system 60 is extending through a first cannula 80A. In certain examples, first cannula 80A can access a treatment site within shoulder 22 using a lateral approach in which first cannula 80A pierces the outer surface of a right side of the patient's body. In some cases a physician may choose not to use a cannula in conjunction with implant delivery system 60. In such examples, the implant delivery system may be advanced through tissue. Implant delivery system 60 comprises a sheath that is affixed to a handle. The sheath defines a lumen and a distal opening fluidly communicating with the lumen. In the example of FIG. 8, the distal opening of the sheath has been placed in fluid communication with the cavity created in shoulder 22.

A tendon repair implant is at least partially disposed in the lumen defined by the sheath of implant delivery system 60. Implant delivery system 60 can be used to place the tendon repair implant inside shoulder 22. In some examples, the tendon repair implant is folded into a compact configuration when inside the lumen of the sheath. When this is the case, implant delivery system 60 may be used to unfold the tendon repair implant into an expanded shape. Additionally, implant delivery system 60 can be used to hold the tendon repair implant against the tendon.

The tendon repair implant may be affixed to the tendon while it is held against the tendon by implant delivery system 60. Various attachment elements may be used to fix the tendon-repair implant to the tendon. Examples of attachment elements that may be suitable in some applications include sutures, tissue anchors, bone anchors, and staples. In the example of FIG. 8, the shaft of a fixation tool 70 is shown extending into shoulder 22. In some examples, fixation tool 70 is capable of fixing the tendon repair implant to the tendon and bone with one or more staples of the present disclosure while the tendon repair implant may be held against the tendon by implant delivery system 60.

Figure 9:
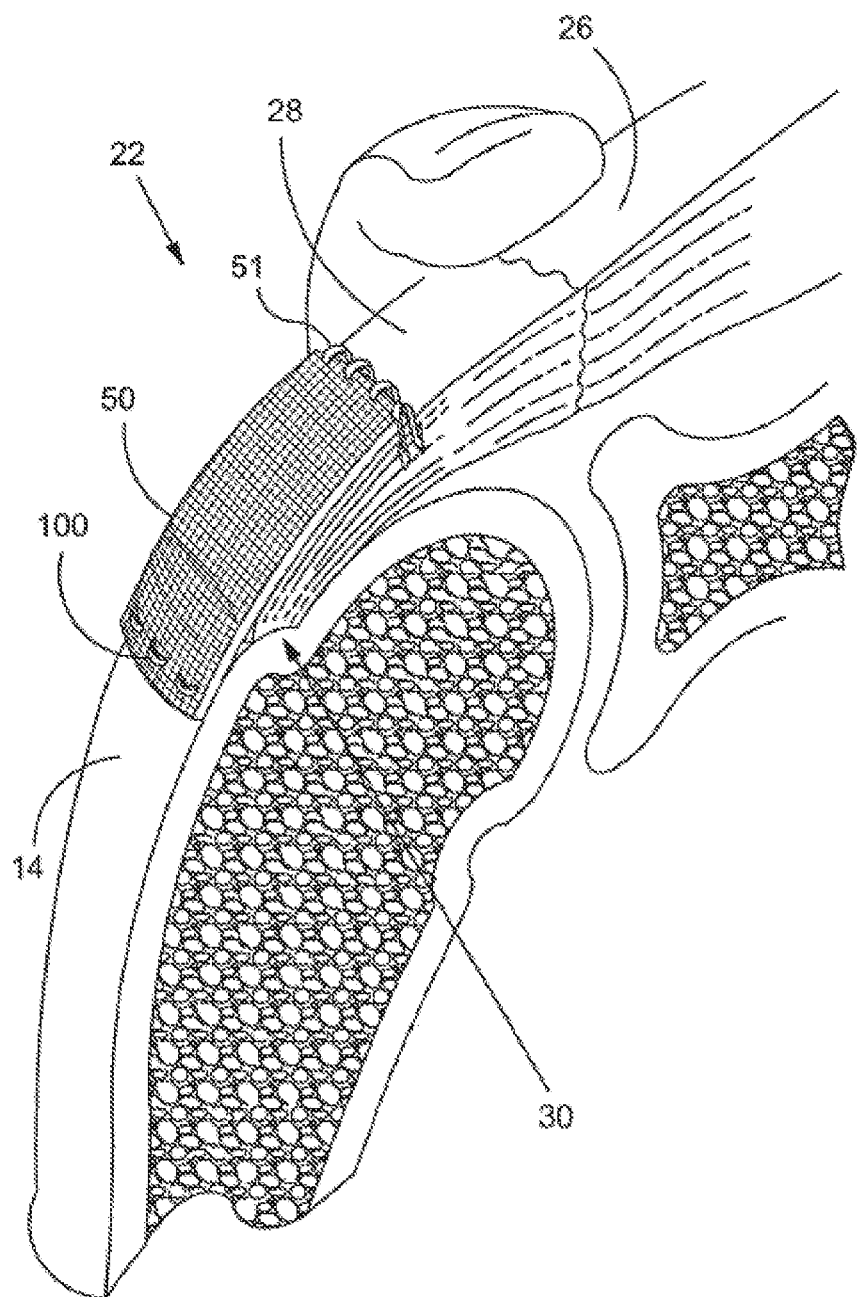
FIG. 9 is a stylized perspective view of a shoulder including a supraspinatus having a distal tendon with a sheet-like material affixed thereto.

FIG. 9 is a stylized perspective view of a shoulder 22 including a supraspinatus 26 having a distal tendon 28. With reference to FIG. 9, a tendon repair implant 50 has been affixed to a surface of distal tendon 28. Tendon repair implant 50 may comprise, for example, various sheet-like structures without deviating from the spirit and scope of the present detailed description. In some examples, the sheet-like structure may comprise a plurality of fibers. The fibers may be interlinked with one another. When this is the case, the sheet-like structure may comprise a plurality of apertures comprising the interstitial spaces between fibers. Various processes may be used to interlink the fibers with one another. Examples of processes that may be suitable in some applications including weaving, knitting, and braiding. In some examples, the sheet-like structure may comprise a laminate including multiple layers of film with each layer of film defining a plurality of micro-machined or formed holes. The sheet-like structure of the tendon repair implant may also comprise a reconstituted collagen material having a porous structure. Additionally, the sheet-like structure of the tendon repair implant may also comprise a plurality of electro-spun nanofiber filaments forming a composite sheet. Additionally, the sheet-like structure may comprise a synthetic sponge material that defines a plurality of pores. The sheet-like structure may also comprise a reticulated foam material. Reticulated foam materials that may be suitable in some applications are available from Biomerix Corporation of Fremont, Calif. which identifies these materials using the trademark BIOMATERIAL™. The sheet-like structure may be circular, oval, oblong, square, rectangular, or other shape configured to suit the target anatomy.

In the examples of FIG. 9, sheet-like implant 50 is affixed to distal tendon 28 by a plurality of tendon staples 51. Sheet-like implant 50 is affixed to humerus 14 by a plurality of bone staples 100 as described with respect to the exemplary embodiment of FIG. 1 and detailed throughout this disclosure. However, in other examples, as described previously, various attachment elements may be used to fix tendon repair implant 50 to distal tendon 28 without deviating from the spirit and scope of this detailed description. Example attachment elements that may be suitable in some applications include sutures, tissue anchors, bone anchors, and staples.

In some exemplary methods, a plurality of staples may be applied using a fixation tool. After the staples are applied, the fixation tool may be withdrawn from the body of the patient. Distal tendon 28 meets humerus 14 at an insertion point 30. With reference to FIG. 9, it will be appreciated that sheet-like implant 50 extends over insertion point 30. Tendon repair implant may be applied to distal tendon 28, for example, using the procedure illustrated in the previous figures. In various examples, staples may straddle the perimeter edge of the sheet-like implant (as shown in FIG. 9), may be applied adjacent to the perimeter, and/or be applied to a central region of the implant. In some examples, the staples may be used to attach the implant to soft tissue and/or to bone.

Staples or fasteners 100, as exemplified in FIG. 1 and described and illustrated herein can be used to attach tissue and implants to bone. In at least some embodiments, the staple is generally flexible and includes areas of relative lateral weakness on the trunks and can further include an increase in flexibility at the transition from the trunk to the non-trunk portion of the arm or the transition from the trunk to the bridge. As described above, these areas of increased flexibility provide improved staple retention as these portions allow flexing and bending in response to increasing pullout forces. With this flexibility, the fasteners cannot be pounded or driven into bone or other tissue as a conventional hard staple would be driven into paper, wood, tissue or bone. Therefore, for application of the staple of the present disclosure to affixing tissue or implants to bone, the staple is generally included in a kit that also includes a staple delivery device 200 and various inserts, including pilot hole forming insert assembly 270 and staple delivery insert assembly 290 as disclosed herein.

Figure 10A:
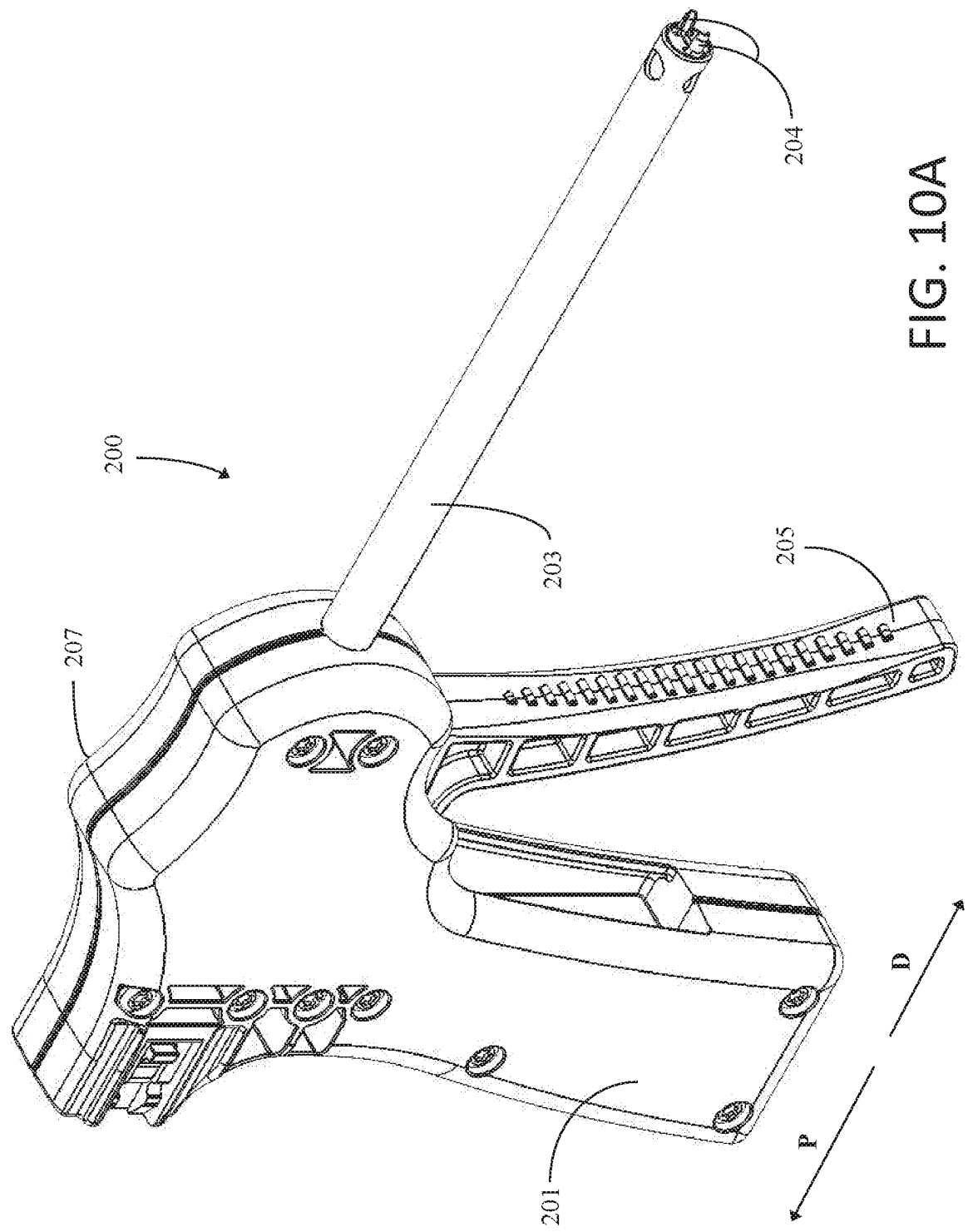
FIG. 10A is a perspective view illustrating an example fastener delivery device in accordance with one example of the present disclosure.
Figure 10B:
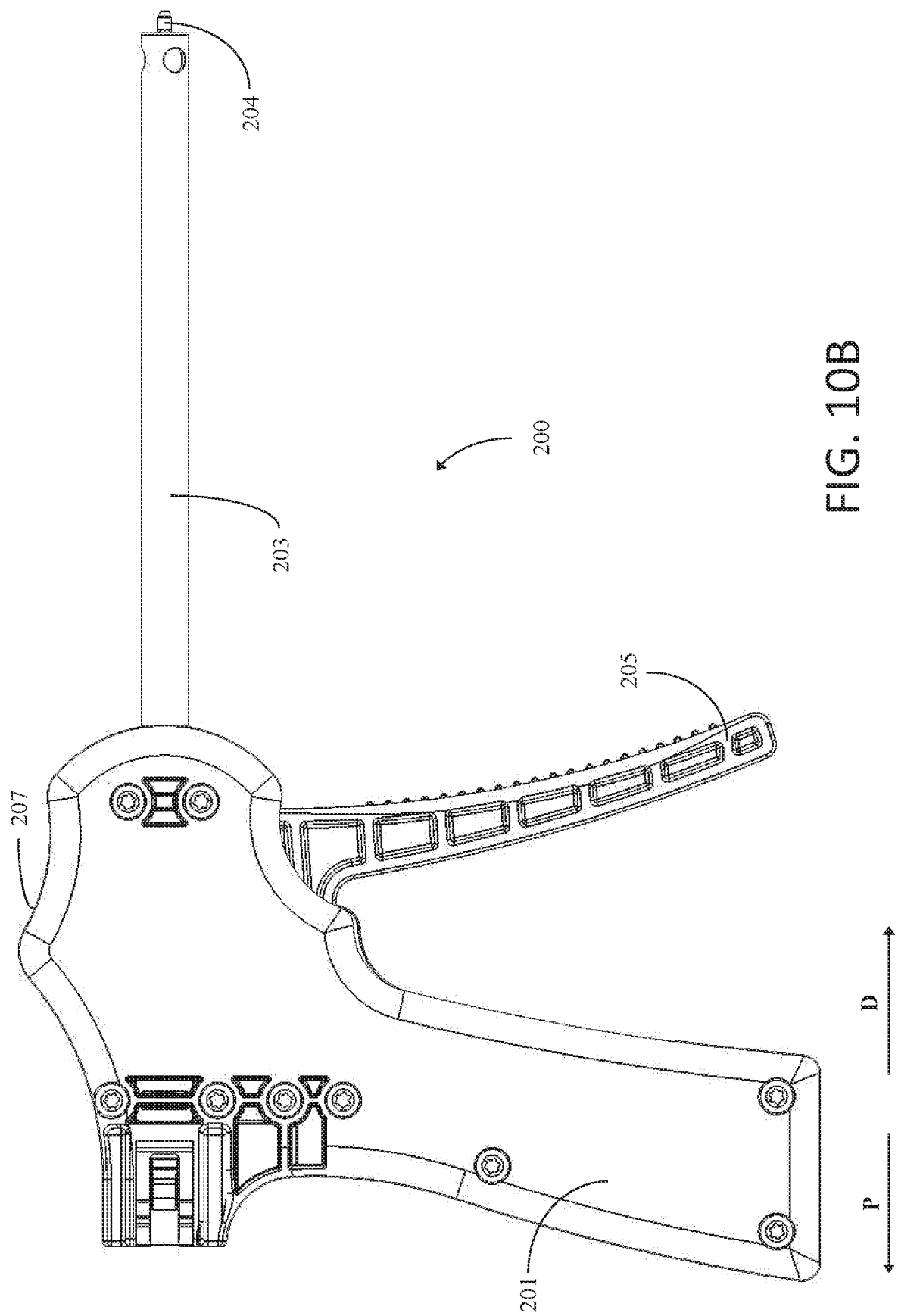
FIG. 10B is a front plan view illustrating an example fastener delivery device in accordance with one example of the present disclosure.

FIGS. 10A and 10B are schematic illustrations depicting two perspective views of staple delivery device 200. As used herein to describe various features of staple delivery device 200, the proximal direction is represented by arrow P in FIGS. 10A and 10B, and the distal direction is represented by arrow D in FIGS. 10A and 10B. In general, staple delivery device 200 comprises handle assembly 201, sheath 203, and position retention members 204. Sheath 203 may be a hollow tube and be configured to receive one or more inserts into its lumen, as described with respect to later figures. Position retention members 204 may be affixed to the distal end of sheath 203. Handle assembly 201 may generally comprise trigger handle 205 and housing 207.

Figure 11:
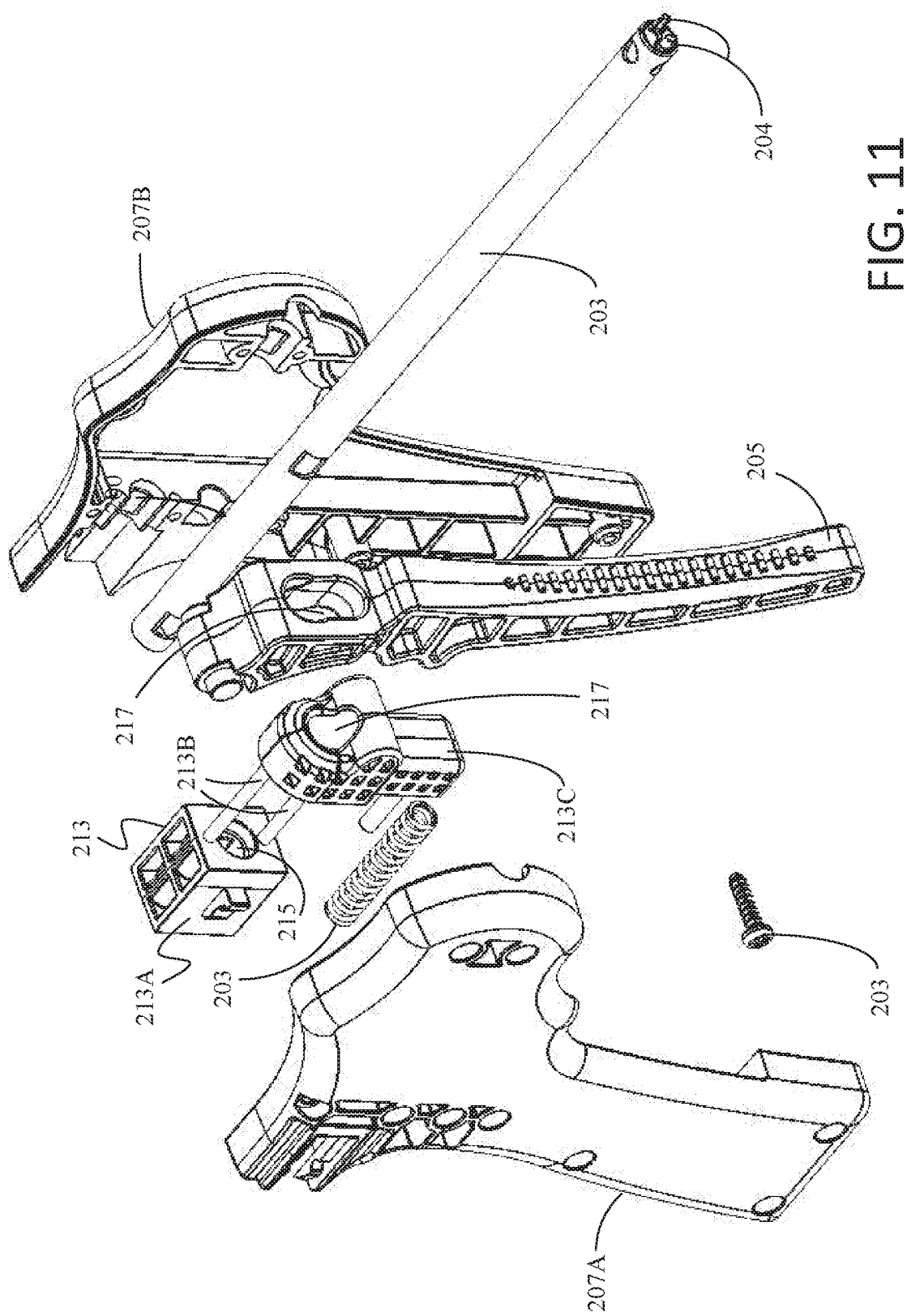
FIG. 11 is an exploded view illustrating an example fastener delivery device in accordance with one example of the present disclosure.

FIG. 11 is another exemplary schematic illustration which depicts staple delivery device 200 in an exploded configuration. Internally, staple delivery device 200 may include spring 211 and insert connector assembly 213. Generally, insert connector assembly 213 may comprise insert connector 213A, connector rods 213B, and cam follower 213C. Insert connector 213A and cam follower 213C may further include openings 215 and 217, respectively. Insert connector 213A may be positioned with respect to sheath 203 such that when sheath 203 receives an insert, the proximal end of the insert is disposed proximate or abuts insert connector 213A. Spring 211 is connected to housing 207 and cam follower 213C. Spring 211 presses cam follower 213C into trigger handle 205, which biases trigger handle 205 to a rest position. In some examples, housing 207 may comprise two halves 207A and 207B. In different examples, halves 207A and 207B may be connected together by various means. In the example of FIG. 11, halves 207A and 207B are connected by screws 209 (only a single screw is shown). However, in other examples, halves 207A and 207B may be connected by glue, rivets, a friction fit, or other means. As evidenced in FIG. 11, trigger handle 205 may additionally include opening 219.

Generally, components of staple delivery device 200 may be made from any rigid material. For example, in different examples, staple delivery device may be made from any of a variety of different metals or metal alloys. Some example metals include the various alloys of stainless steel. In other examples, staple delivery device 200 may be constructed from plastic. In such examples, the plastic may generally be rigid and resist deformation. Some example plastics include polymers such as Nylon 12, Polyethylene terephthalate (PET), polybutylene terephthalate (PBT), Polyamide 12, Polyether block amide (PEbax) 7233, Pebax 7033, PTFE, Polyaryletherketones (PEEK), Polyphenylene Oxide (PPO), high density polyethylene (HDPE) and the like. In still other examples, staple delivery device may be constructed from Ixef plastics, which generally include glass fiber reinforcement in addition to one or more polymers. In still other examples, some portions of staple delivery device 200 may be constructed from plastic, such as housing 207, insert connector assembly 213, and trigger handle 205, and other portions of staple delivery device 200 may be constructed from metal, such as sheath 203. Of course, in other examples, other combinations of components of staple delivery device 200 may be made from plastic and metal.

Figure 12:
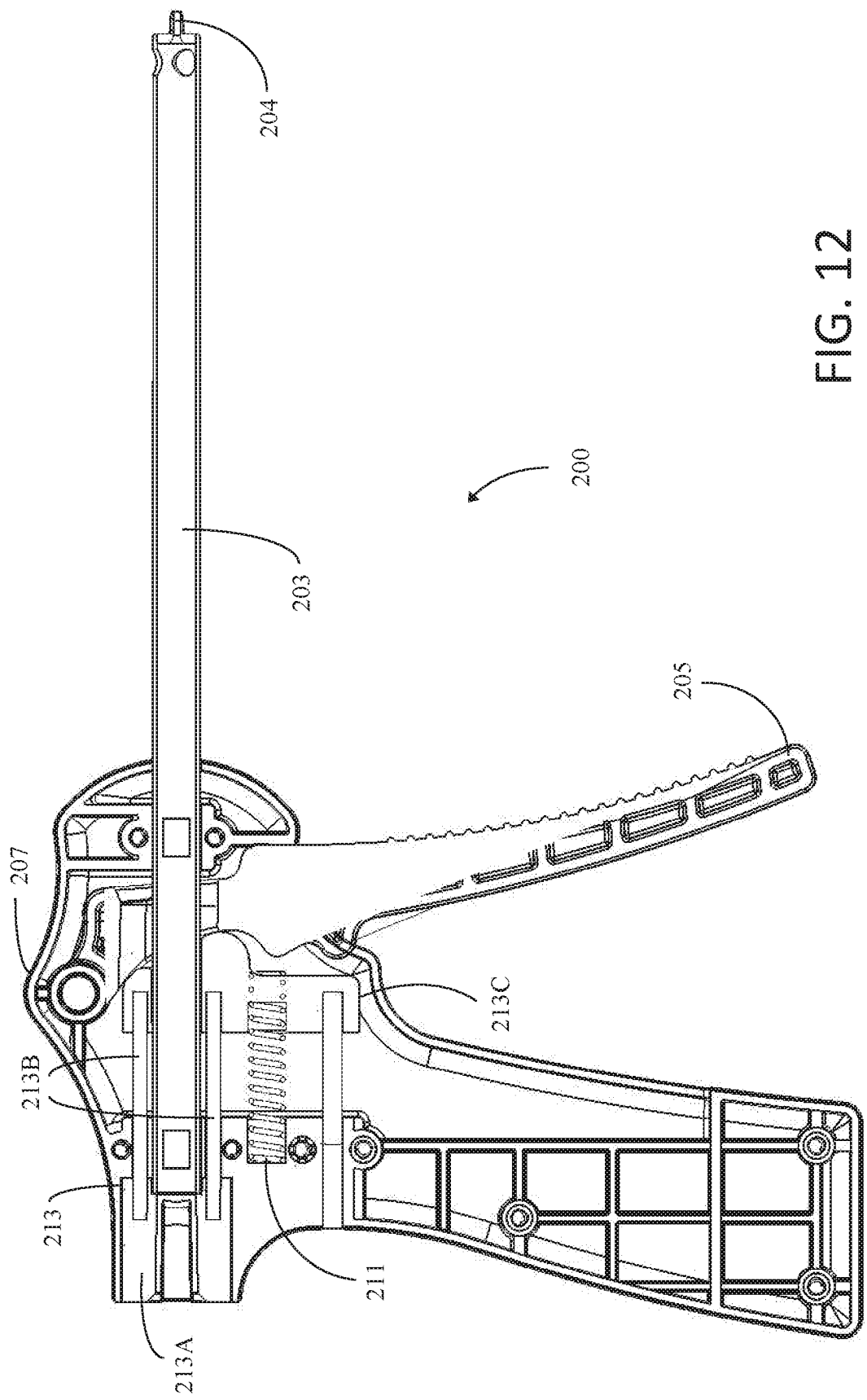
FIG. 12 is a cross section view illustrating internal components of an example fastener delivery device in accordance with one example of the present disclosure.

FIG. 12 is another internal view of staple delivery device 200 depicting trigger handle 205 at the rest position. FIG. 12 more clearly shows the configuration of spring 211 with respect to cam follower 213C and trigger handle 205.

Figure 13:
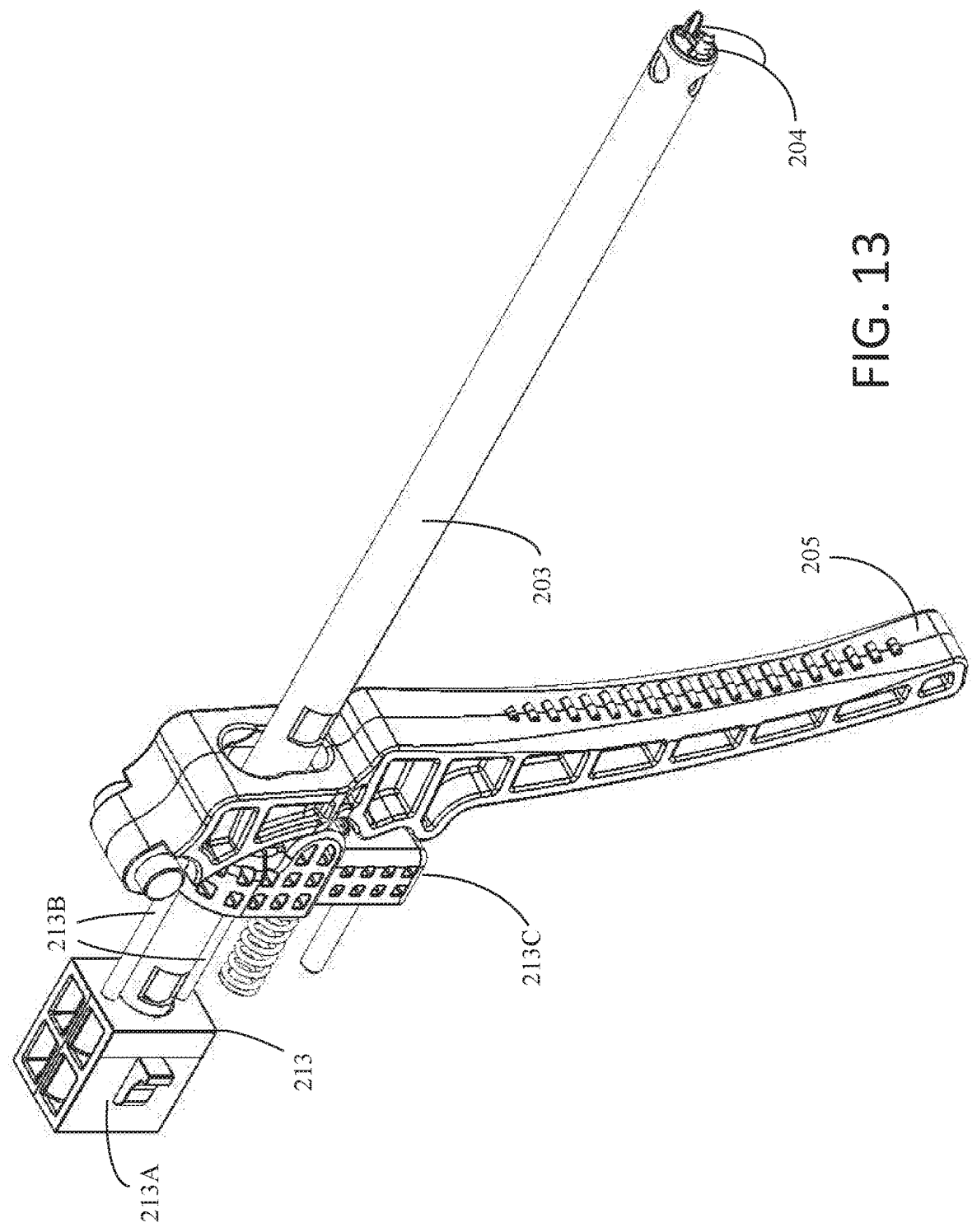
FIG. 13 is a schematic view illustrating internal components of an example fastener delivery device in accordance with one example of the present disclosure.

FIG. 13 is a further schematic illustration of staple delivery device 200. FIG. 13 depicts how sheath 203, trigger handle 205, and insert connector assembly 213 are disposed together within staple delivery device 200. When assembled, as seen in FIG. 13, sheath 203 may be disposed through openings 215, 217 of insert connector 213A and cam follower 213C, respectively, and opening 219 of trigger handle 205.

As described previously, when sheath 203 has received an insert, the proximal end of the insert may be disposed proximate or abut insert connector assembly 213, and more specifically insert connector 213A. When force is applied in the proximal direction to trigger handle 205, the applied force is transferred to insert connector 213A through cam follower 213C and connector rods 213B. The transferred force causes insert connector 213A to translate in the proximal direction, thereby applying force in the proximal direction to the proximal end of the received insert. The applied force on the received insert thereby causes the received insert to move in the proximal direction. After squeezing trigger handle 205 to initially move a received insert in the proximal direction, a user may then grasp the proximal end of the received insert to remove the insert from the lumen of sheath 203.

In some examples, various forces may be attempting to retain the received insert in sheath 203. For example, as will be described with respect to later figures, at least one insert may have one or more members (e.g. pilot hole forming members) configured to pierce tissue or bone. Due to the physical makeup of the tissue or bone, the tissue or bone may apply squeezing forces to the one or more members, thereby causing the tissue or bone to retain the one or more members. In such examples, the actions of trigger handle 205 and insert connector assembly 213 may provide mechanical means for removing the one or more members from the retaining forces of the tissue or bone. Such mechanical means may be easier for a user than grasping at the proximal end of the received insert and attempting to pull the one or more retaining members out of the tissue or bone.

In some examples, the force required to remove the one or more members from tissue or bone may be above what a user is comfortably able to apply to trigger handle 205. Accordingly, staple delivery device 200 may employ mechanical advantage to multiply or otherwise increase the force applied by a user of staple delivery device 200. FIGS. 14-17 depict the internal workings of staple delivery device 200, which may operate to multiply or otherwise increase the force applied to trigger handle 205 and transfer the increased force onto the proximal end of a received insert. FIGS. 14-17 all have various components of staple delivery device 200 removed for easier viewing of the described components.

In addition to showing the internal components of staple delivery device 200, FIG. 12 shows trigger handle 205 in the rest position. That is, no force is being applied to trigger handle 205 in the proximal direction, and spring 211 is biasing trigger handle 205 in the rest position. Spring 211 biases trigger handle 205 to the rest position by applying force to cam follower 213C in the distal direction which, in turn, applies force in the distal direction to trigger handle 205.

Figure 14:
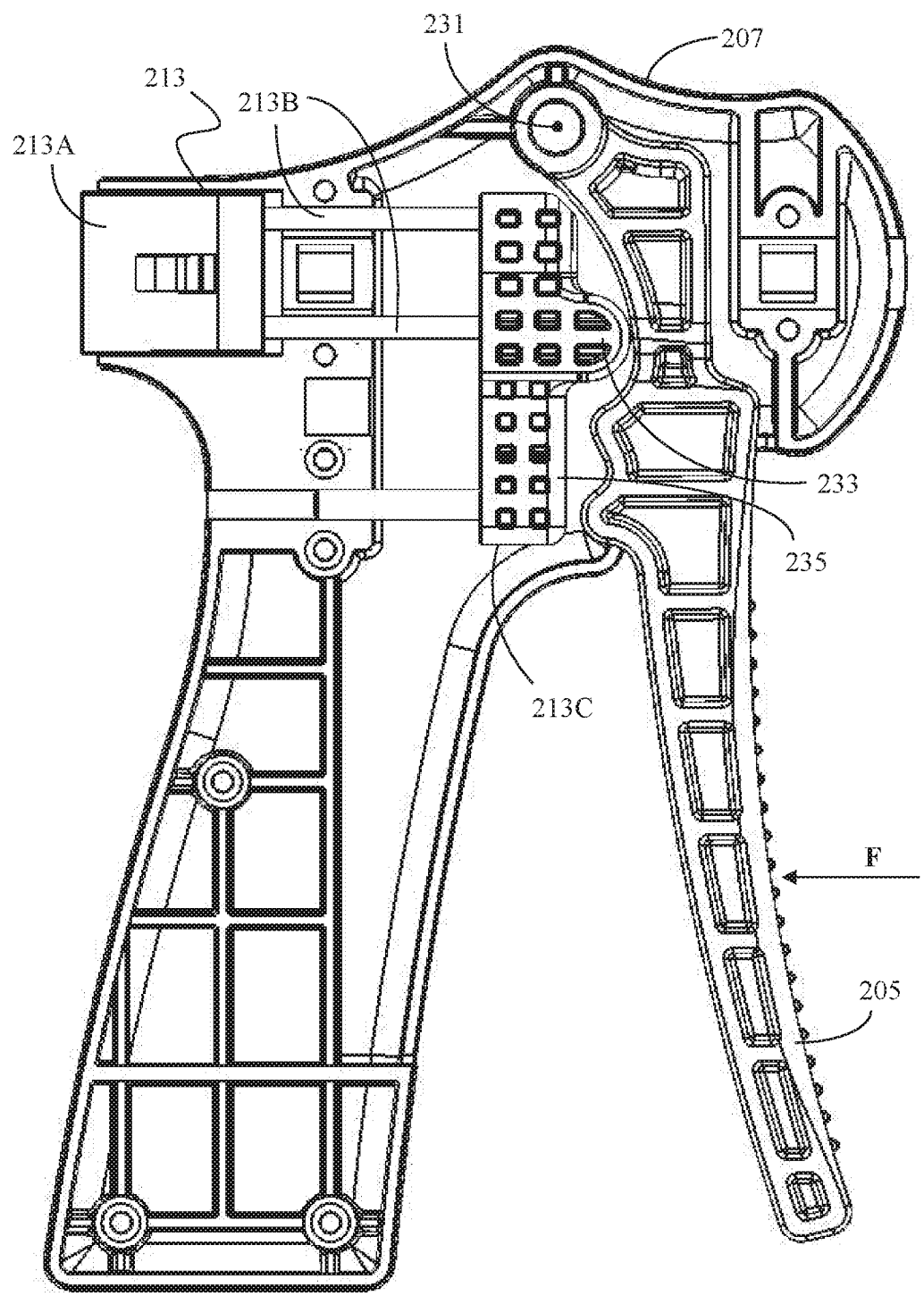
FIGS. 14-17 are schematic illustrations depicting the positions of select internal components of an example fastener delivery device in accordance with one example of the present disclosure as force is applied to the trigger handle of the device.

FIG. 14, then, is an example schematic of staple delivery device 200 after force has been applied in the proximal direction to trigger handle 205 sufficient to overcome the biasing force of spring 211. As can be seen in the differences between FIG. 12 and FIG. 14, trigger handle 205 is rotatably attached to housing assembly 201 at rotation point 231. In such an example, applying a force to trigger handle 205 in the proximal direction, as indicated by arrow F, may cause trigger handle 205 to rotate about rotation point 231 in the proximal direction. Additionally, as can be seen FIG. 14, cam follower 213C comprises protrusion 233 and flat portion 235. In the rest position, protrusion 233 of cam follower 213C is in contact with trigger handle 205, while flat portion 235 is not in contact with trigger handle 205. As trigger handle initially rotates in response to an applied force, trigger handle 205 pushes on protrusion 233. The force applied to protrusion 233 is then transferred to insert connector 213A through connector rods 213B. The transferred force on insert connector 213A causes insert connector 213A to translate in the proximal direction, as is evidenced by a portion of insert connector 213A extending beyond the proximal end of housing 207 in FIG. 14.

Figure 15:
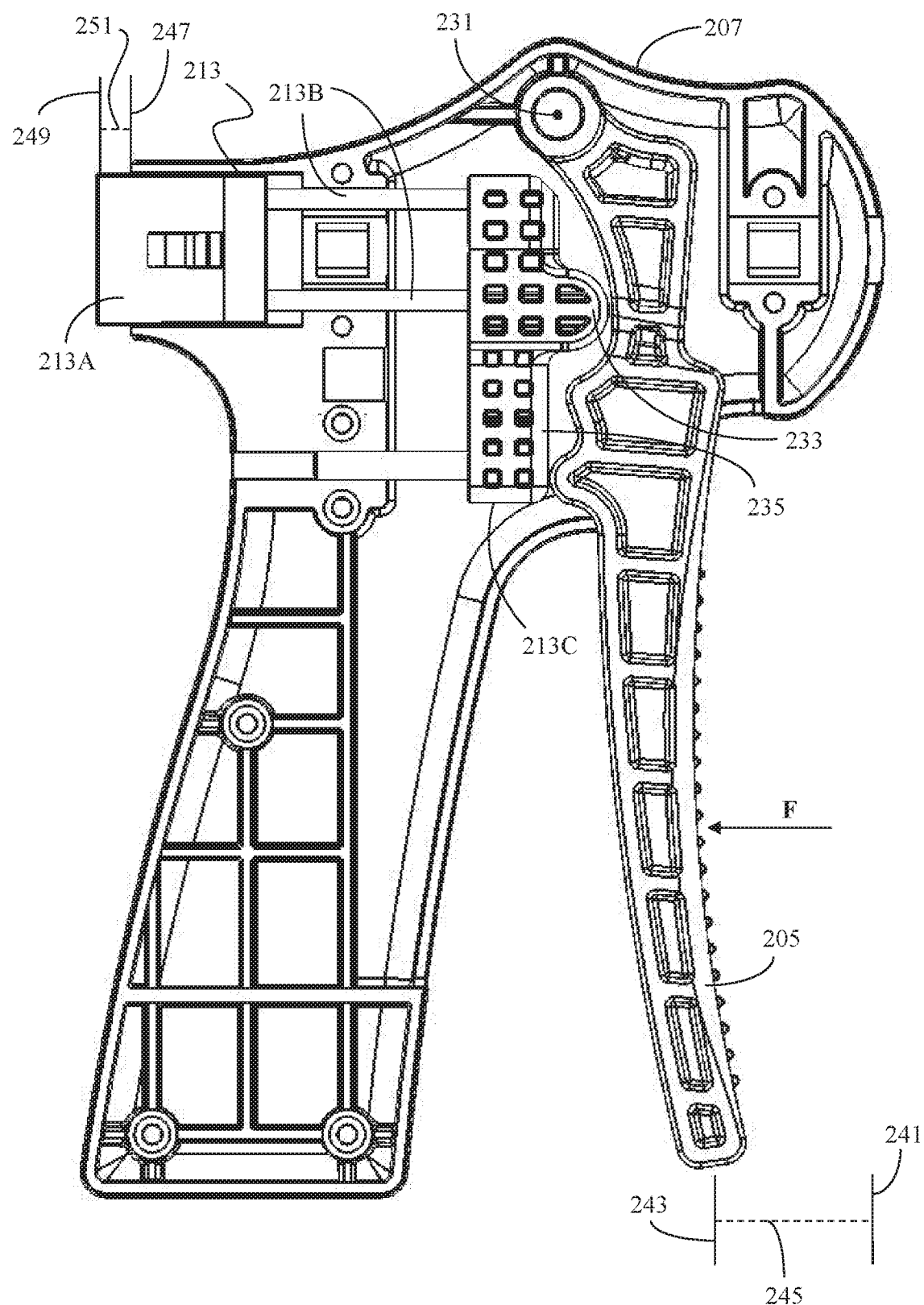

FIG. 15 depicts some of the internal components of staple delivery device 200 when the internal components are at a transition point. As can be seen in FIG. 15, and in contrast to FIG. 14, both protrusion 233 and flat portion 235 of cam follower 213C contact trigger handle 205. FIG. 15 further depicts initial positions 241, 247 and transition positions 243, 249 of trigger handle 205 and insert connector 213A, respectively. As can be seen, first translation distance 245 of trigger handle 205 with respect to initial position 241 and transition position 243 is greater than first translation distance 251 of insert connector 213A with respect to initial position 247 and transition position 249. The displacement ranges of trigger 205 from initial position 241 up to transition position 243 correspond to a first range of displacements where staple delivery device 200 is operating in a first mechanical advantage stage.

In the first mechanical advantage stage, the force applied to trigger handle 205, such as by a user, may be multiplied between two and six times as the applied force is transferred to insert connector 213A due to the action of trigger handle 205 pressing against cam follower 213C, and more specifically protrusion 233 of cam follower 213C. In some examples, the force applied to trigger handle 205 may be multiplied by four times and transferred to connector 213A. The multiplication of the force applied to trigger handle 205 in this first mechanical advantage stage, and correspondingly to a proximal end of a received insert, may help to remove any members of a received insert that are embedded in tissue or bone.

Figure 16:
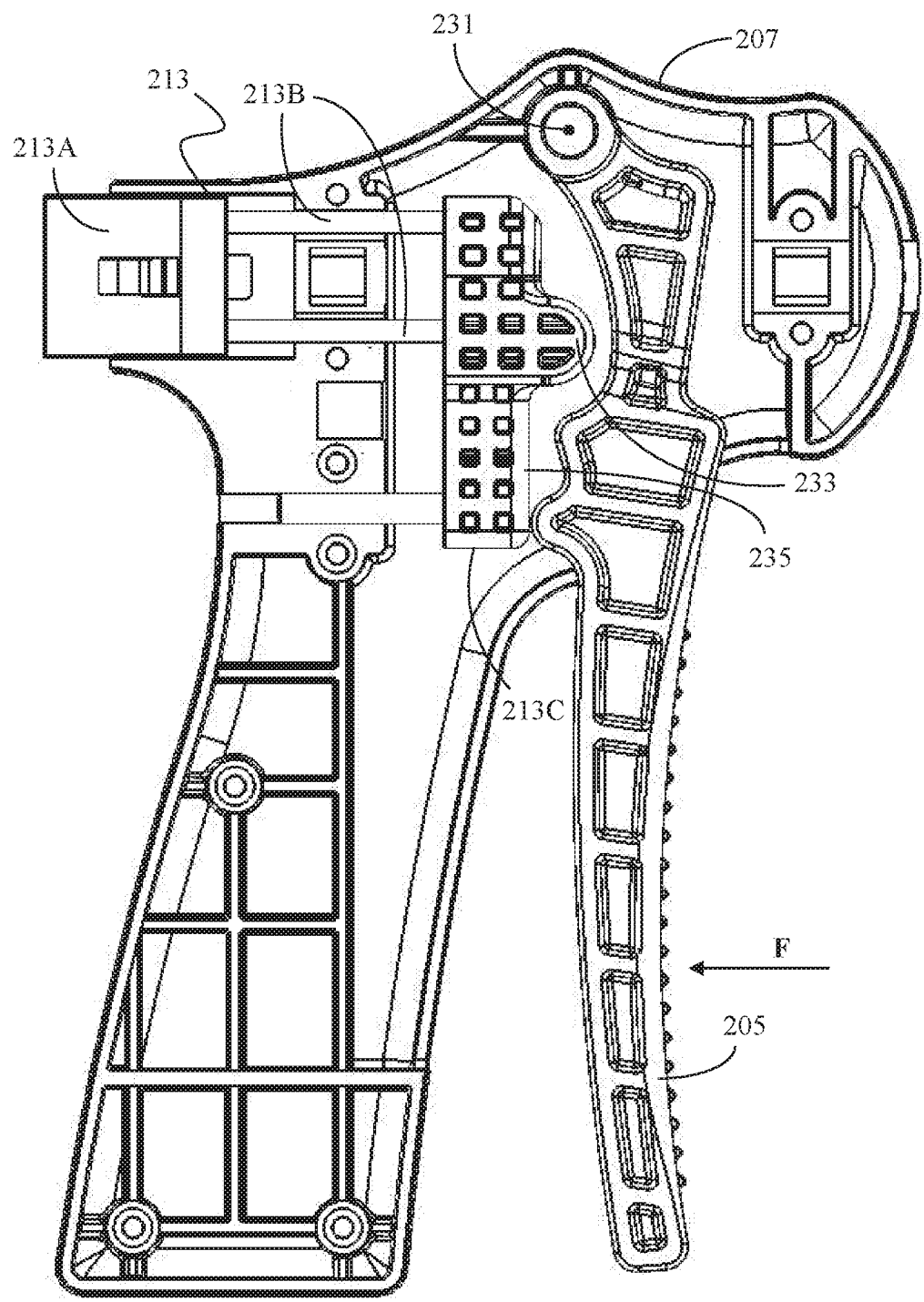

FIG. 16 depicts some of the internal components of staple delivery device 200 after trigger handle 205 has been rotated past the transition point depicted in FIG. 15. In FIG. 16, in contrast to FIGS. 14 and 15, only flat portion 235 of cam follower 213C contacts trigger handle 205. As force is continued to be applied to trigger handle 205, trigger handle 205 will continue to rotate about rotation point 231 until insert connector 213A presses against housing 207, as depicted in FIG. 17.

Figure 17:
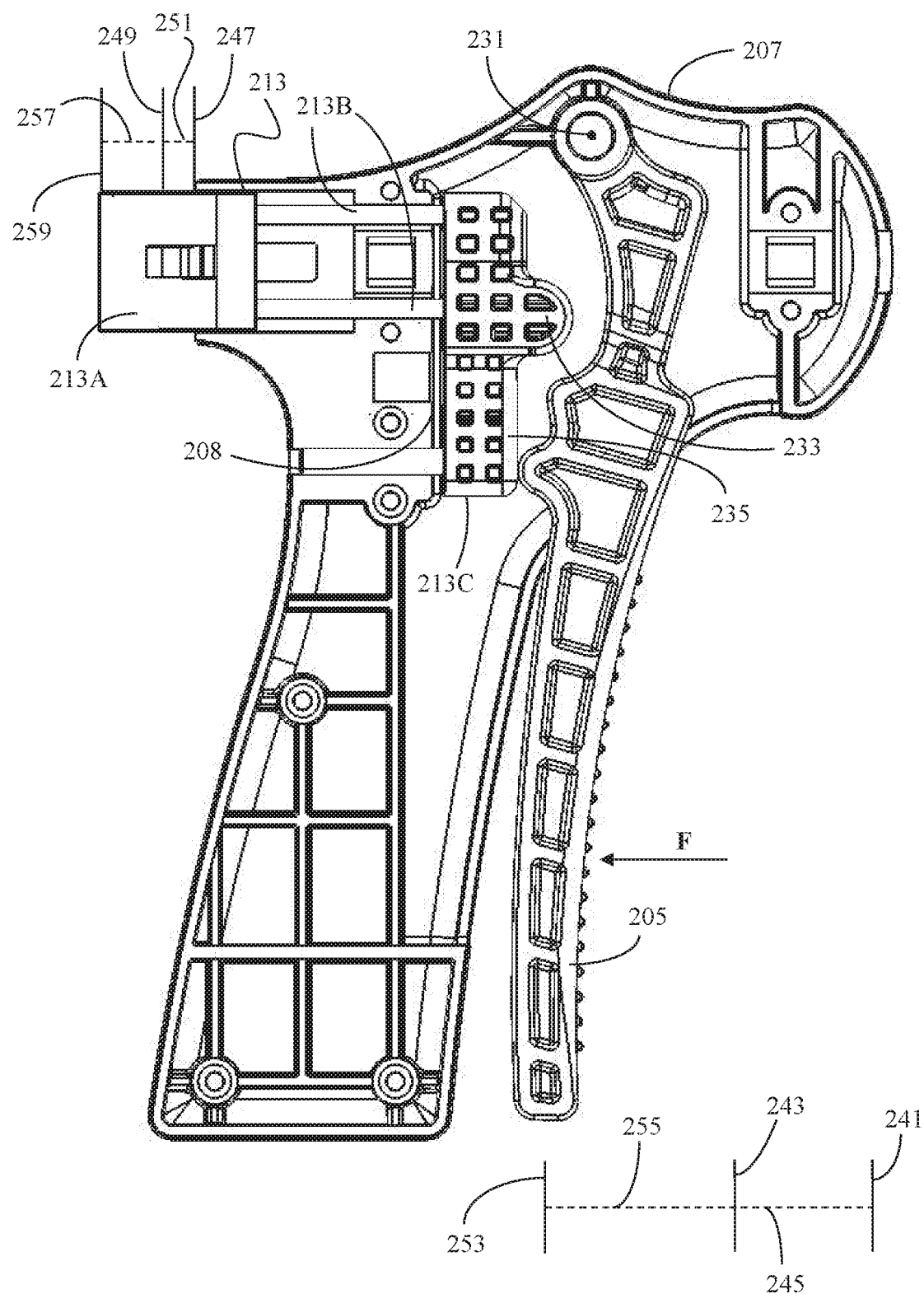

FIG. 17 depicts some of the internal components of staple delivery device 200 when the internal components are at a stop point. In the depiction of FIG. 17, trigger handle 205 may not be rotated any more about rotation point 231 as insert connector 213A is in contact with housing 207 along housing edge 208. FIG. 17 further depicts initial positions 241, 247, transition positions 243, 249, and stop positions 253, 257 of trigger handle 205 and insert connector 213A, respectively. The displacement ranges of trigger handle 205 from transition position 243 up to stop position 253 correspond to a second range of displacements where staple delivery device 200 is operating in a second mechanical advantage stage.

In the second mechanical advantage stage, the force applied to trigger handle 205, such as by a user, may be multiplied between one and four times as the force is transferred to insert connector 213A, and ultimately a proximal end of a received insert, due to the action of trigger handle 205 pressing against cam follower 213C, and more specifically flat portion 235 of cam follower 213C. Generally, the amount of force multiplication in the second mechanical advantage stage may be less than the amount of force multiplication in the first mechanical advantage stage. As another way to relate the two mechanical advantage stages, during the first mechanical advantage stage, the force applied to insert connector 213A may be between two and four times the force applied to insert connector 213A during the second mechanical advantage stage for a given force applied to trigger handle 205. In at least some examples, during the first mechanical advantage stage, the force applied to insert connector 213A may be three times the force applied to insert connector 213A during the second mechanical advantage stage, for a given force applied to trigger handle 205.

While during the first mechanical advantage stage the force multiplier is generally greater than during the second mechanical advantage stage, in some examples, the translation distance of insert connector 213A during the first mechanical advantage stage may generally be less than the translation distance of insert connector 213A during the second mechanical advantage stage. This feature can be seen in FIG. 17 where second translation distances 255, 259 of trigger handle 205 and insert connector 213A, respectively, are generally greater than first translation distances 245, 251. In this manner, staple delivery device 200 may operate to multiply force applied to trigger handle 205 yet still allow for sufficient translation of a received insert to remove any members that are disposed within bone or tissue. This type of action may assist a user in removing a received insert from the lumen of sheath 203.

In other examples, the values of first translation distances 245, 251 relative to second translation distances 255, 257 may be different than that described with respect to FIGS. 15-17. For instance, in some examples, first translation distances 245, 251 may be equal to second translation distances 255, 257. However, in other examples, first translation distances 245, 251 may be greater than second translation distances, 255, 257. In some specific examples, first translation distances 245, 251 may be ninety percent of the total possible translation distances of handle 205 and insert connector 213A, which is equal to the addition of first and second translation distances 245 and 255 for handle 205 and first and second translation distances 251, 257 of insert connector 213A.

In still other examples, the relative values of first translation distance 245 to second translation distance 255 of handle 205 and first translation distance 251 to second translation distance 257 of insert connector 213A. For instance, in some examples first translation distance 245 may be greater than second translation distance 255 yet first translation distance 251 may be less than second translation distance 257. Conversely, in other examples first translation distance 245 may be less than second translation distance 255 while first translation distance 251 is greater than second translation distance 257.

In accordance with techniques of the present disclosure, a user may employ staple delivery device 200 to deploy one or more staples, such as staples 100, to attach an implant to bone or tissue, as in the example procedure of FIGS. 7-9. Continuing the example of FIGS. 7-9, after a user has prepped the implant area and disposed the implant proximate the implant site, a user may use staple delivery device 200 to deploy one or more staples to attach the implant to the implant site.

Figure 18:
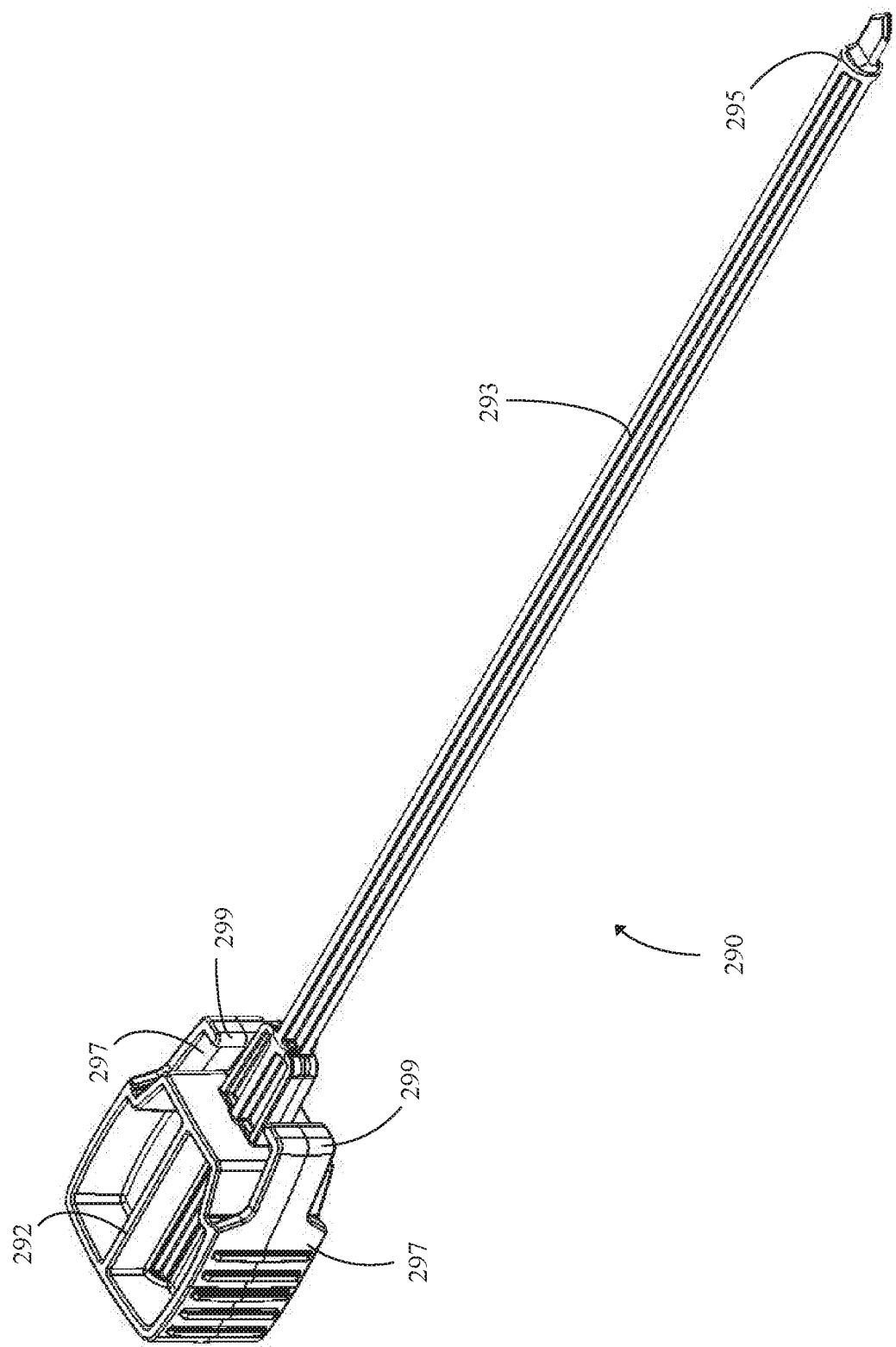
FIG. 18 is a schematic illustration depicting an example retention member sheath insert in accordance with one example of the present disclosure.

FIG. 18 depicts an example schematic illustration of retention member sheath insert 290. In examples where a user does not use a cannula in conjunction with staple delivery device 200, position retention members 204 may catch on tissue as the user maneuvers staple delivery device 200 to the implant site and cause unwanted damage to tissue of the patient. In such examples, a user may use insert 290 to prevent position retention members 204 from catching on tissue.

Figure 19:
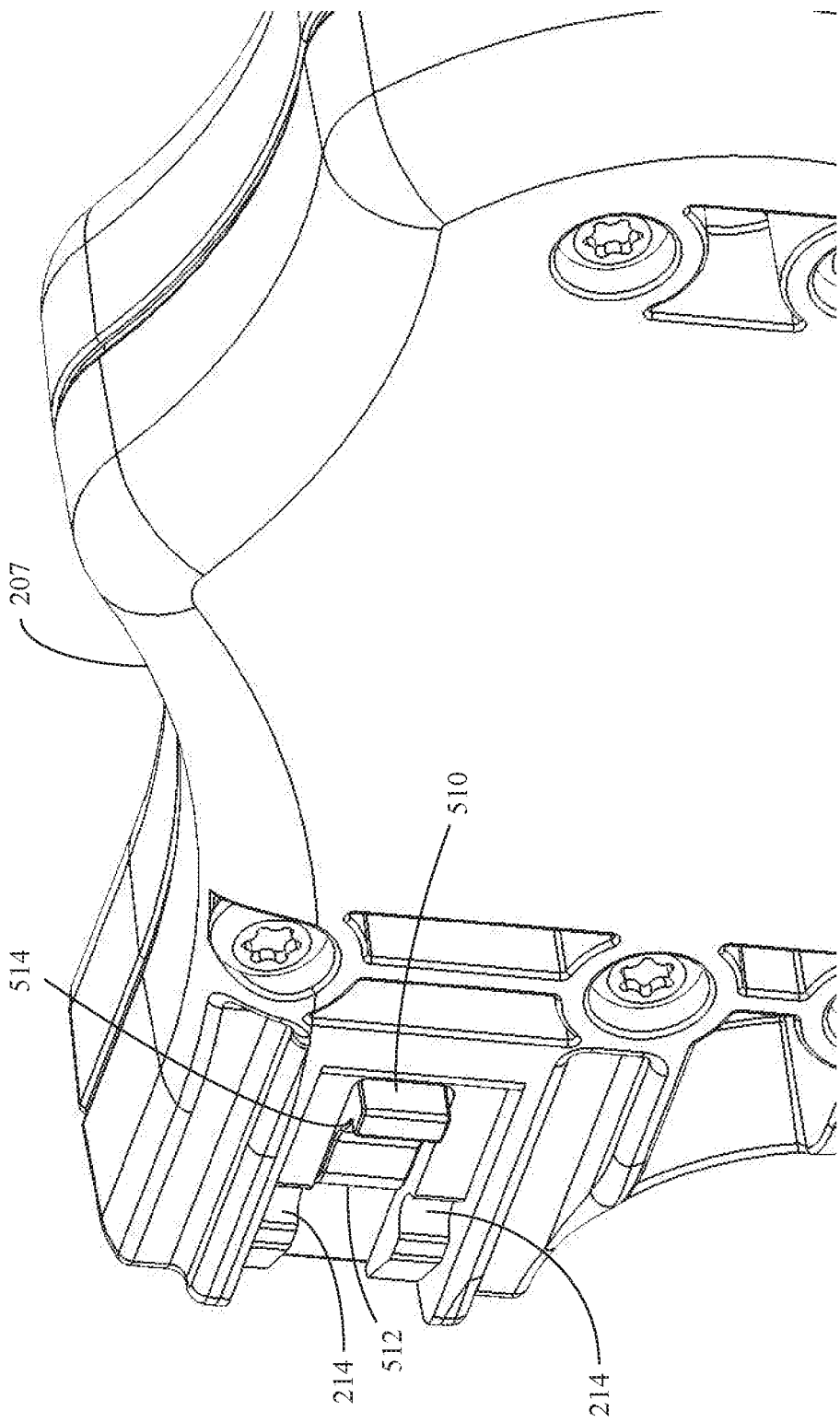
FIG. 19 is a schematic illustration depicting a proximal portion of an example fastener delivery device in accordance with one example of the present disclosure.
Figure 20:
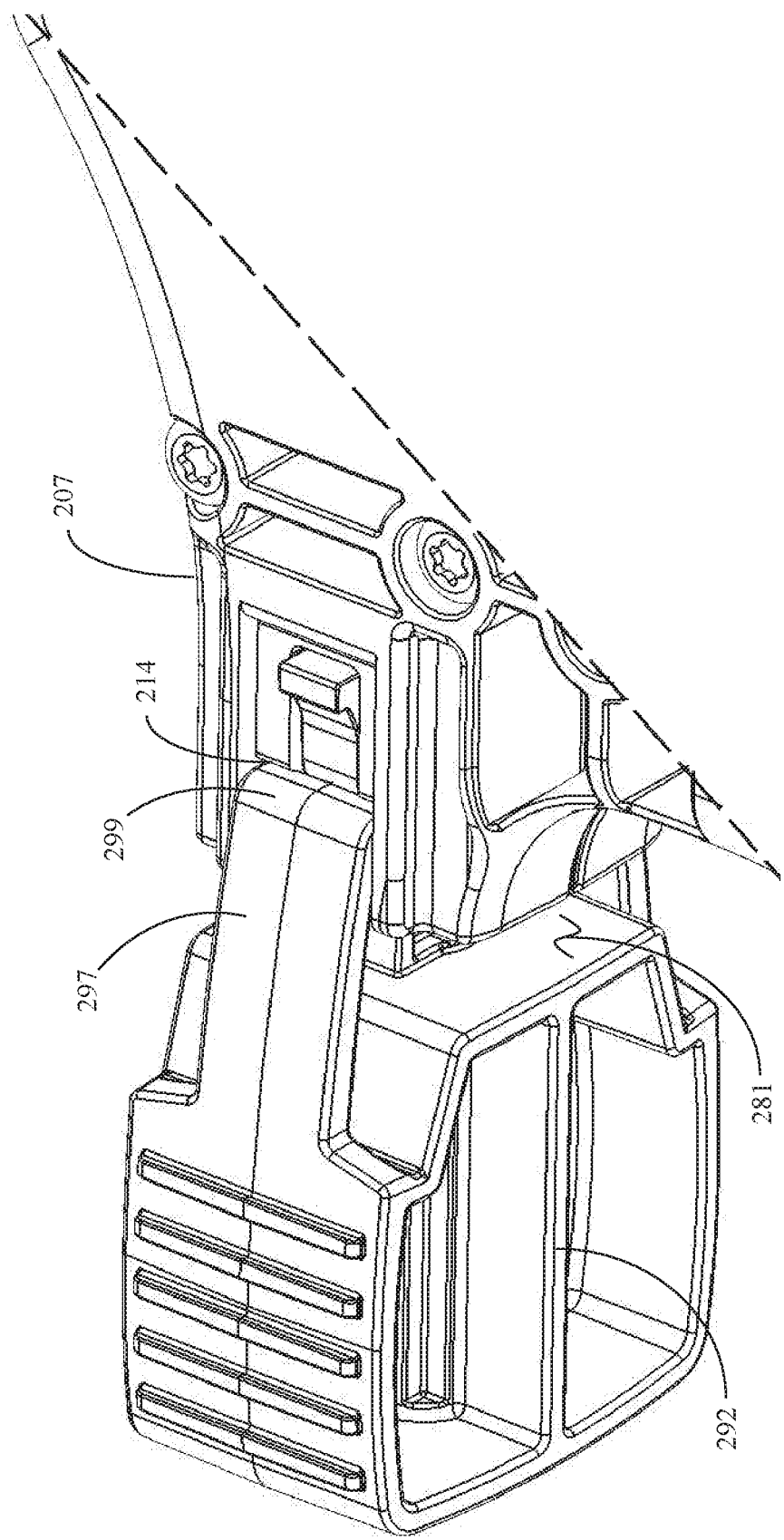
FIG. 20 is a schematic illustration depicting a proximal portion of an example fastener delivery device in accordance with one example of the present disclosure and a proximal head of an example insert when the insert is received within a sheath of the example fastener delivery device.

Insert 290 generally comprises proximal head 292, shaft 293, and distal end 295. When insert 290 is received within sheath 203, shaft 293 may be disposed within the lumen of sheath 203. Proximal head 292 may be disposed proximate or abut insert connector assembly 213 and, more specifically, insert connector 213A. In some examples, proximal head 292 may have connecting fins 297 extending lengthwise down insert 290 toward distal end 295. Connecting fins 297 may additionally have inward facing protrusions 299. As a user inserts insert 290 into sheath 203, inward facing protrusions 299 may slide into grooves 214 of housing 207, securing insert 290 to staple delivery device 200. FIGS. 19 and 20 more clearly show grooves 214 of housing 207 and how inward facing protrusions 299 engage with grooves 214. In some examples, when inward facing protrusions 299 engage with grooves 214 a gap, such as gap 281, may be left between proximal head 292 and housing 207.

Figure 21:
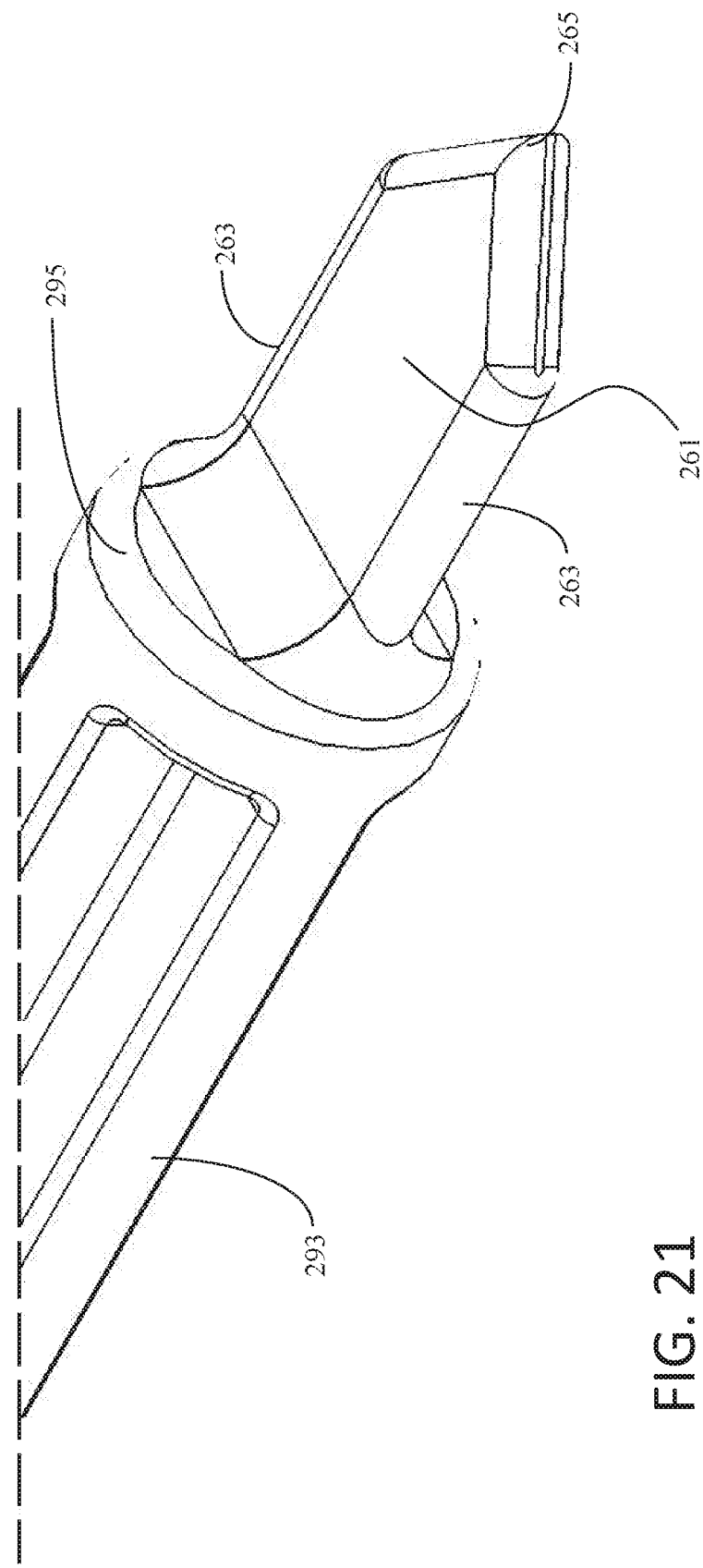
FIG. 21 is a schematic illustration depicting a distal portion of an example retention member sheath insert in accordance with one example of the present disclosure.
Figure 22:
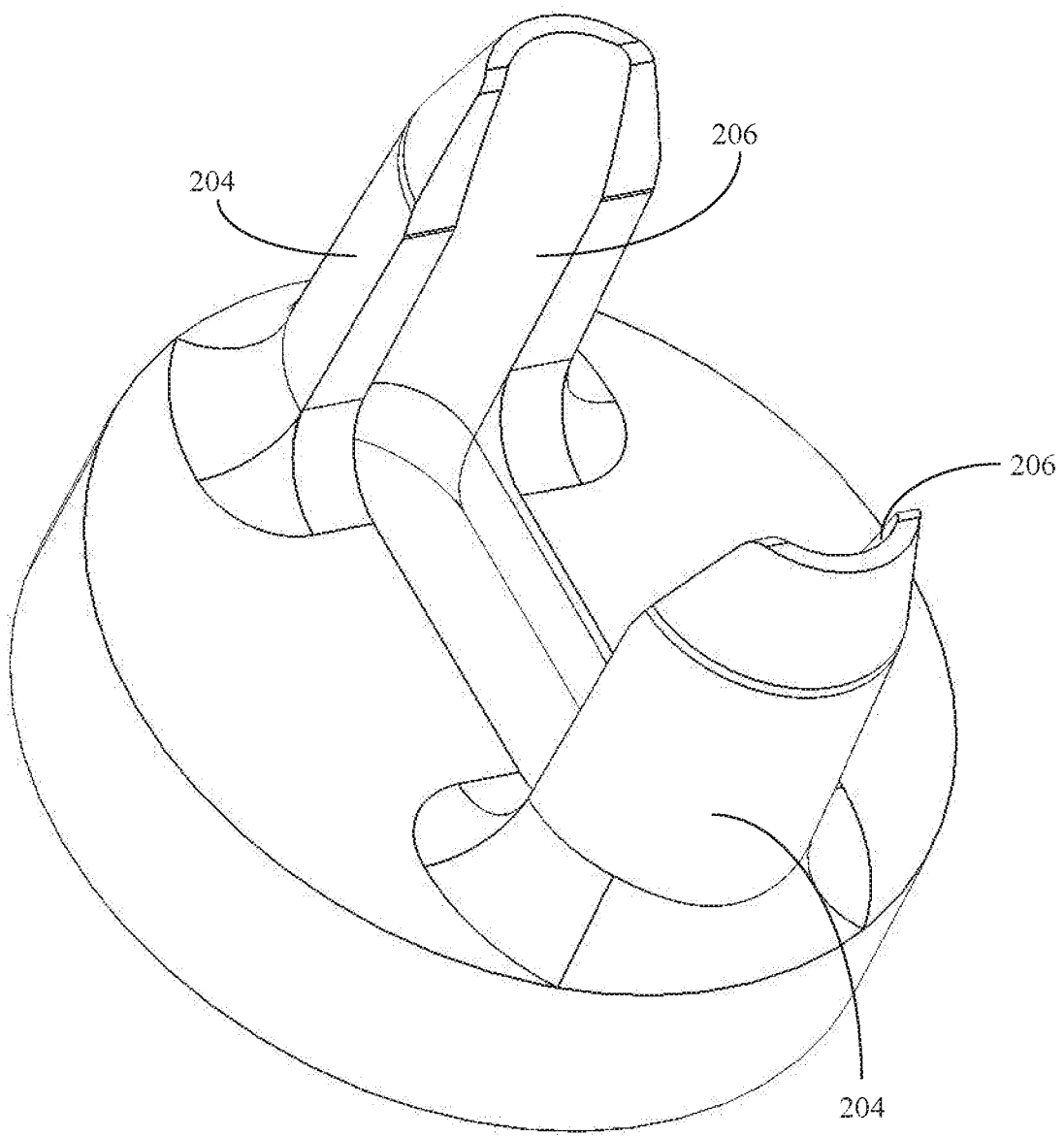
FIG. 22 is a schematic illustration depicting position retention members of an example fastener delivery device in accordance with one example of the present disclosure.

FIG. 21 is a close-up of distal end 295 of insert 290. Attached to distal end 295 of insert 290 is retention member sheath 261. Generally, retention member sheath 261 comprises curved sides 263 and head 265. Curved sides 263 are configured to mate with position retention members 204. FIG. 22 depicts position retention members 204 in a close-up fashion. In some examples, position retention members 204 include curved sides 206. In such examples, curved sides 263 of retention member sheath 261 are configured to mate with curved sides 206 of position retention members 204. When insert 290 is received within sheath 203, head 265 extends beyond the distal end of position retention members 204. Head 265 may come to a point, as depicted in FIG. 19, but may also comprise curved surfaces adjacent to the point. When a user inserts staple delivery device 200 with insert 290 connected into tissue of a patient, head 265 may operate to part cut or uncut tissue. The tissue may then slide around the curved surfaces of head 265 and along curved surfaces 263, allowing the user to advance staple delivery device 200 through the tissue without any portions of staple delivery device 200 catching on tissue. As the user continues to advance staple delivery device 200 into the patient, tissue may slide along curved surfaces 263 and past position retention members 204. In this manner, a user may maneuver staple delivery device 200 to an implant site without catching position retention members 204 on tissue of the patient causing unwanted tissue damage.

Once the user has positioned staple delivery device 200, and more specifically the distal end of sheath 203, near the implant site, the user may remove insert 290. As described previously, to remove insert 290, a user may squeeze trigger handle 205. The action of the internal components of staple delivery device 200 may cause insert connector 213A to push against proximal head 292 of insert 290. The force against proximal head 292 may cause inward facing protrusions 299 to disengage from grooves 214. A user may additionally grasp proximally extended proximal head 292 of insert 290 and completely remove insert 290 from the lumen of sheath 203.

In some examples, insert connector 213A may further comprise disengaging mechanism 510, as depicted in FIG. 19. Disengaging mechanism 510 may include curved surface 512 and ramp 514. When a user squeezes trigger handle 205, insert connector 213A may move in a proximal direction (toward proximal head 292 as seen in FIG. 20). When inward facing protrusions 299 are engaged in grooves 214 and a user squeezes trigger handle 205, curved surface 512 may come in contact with inward facing protrusions 299 as insert connector 213A moves in the proximal direction. As curved surface 512 contacts inward facing protrusions 299, inward facing protrusions 299 may slide up curved surface 512. As the user continues to squeeze trigger handle 205, inward facing protrusions 299 may continue to slide along disengaging mechanism 510 and begin to contact ramp 514, as insert connector 213A continues to move in the proximal direction. As inward facing protrusions 299 begin to contact ramp 514, inward facing protrusions 299 may begin to slide up ramp 514. The action of both curved surface 512 and ramp 514 may cause inward facing protrusions 299 to at least partially lift out of groove 214. In such examples, a user may need to apply relatively less force on trigger handle 205 in order to remove inward facing protrusions 299 from groove 214 than if insert connector 213A did not include disengaging mechanism 510. In some examples, curved surface 512 and ramp 514 may be positioned on insert connector 213A such that the proximal end of insert connector 213A may not begin to press against proximal head 292 of insert 290 until inward facing protrusions 299 have at least slid up curved surface 512. In other examples, curved surface 512 and ramp 514 may be positioned on insert connector 213A such that the proximal end of insert connector 213A may not begin to press against proximal head 292 of insert 290 until inward facing protrusions 299 have slid at least partially up ramp 514.

Figure 23:
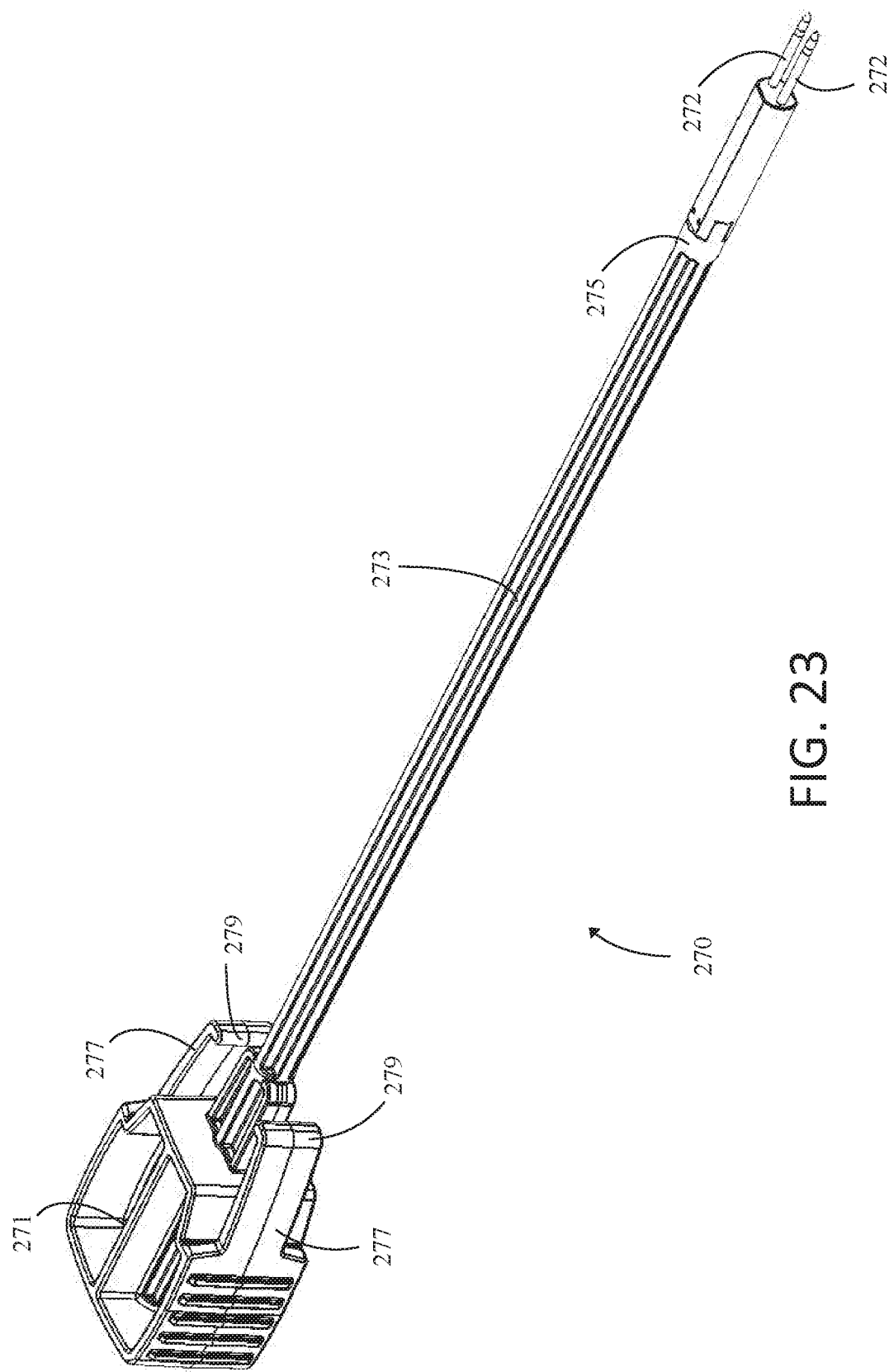
FIG. 23 is a schematic illustration depicting an example pilot hole forming insert in accordance with one example of the present disclosure.

Once insert 290 has been removed, the user may insert pilot hole forming insert 270 into the lumen of sheath 203. FIG. 23 is a schematic illustration of pilot hole forming insert 270. Generally, insert 270 may appear similar to insert 290 and may have proximal head 271, shaft 273, and distal end 275. However, instead of head 261, insert 270 may have one or more pilot hole forming members 272 connected to distal end 275. In different examples, pilot hole forming members 272 may take various different shapes, such as spikes, spears, prongs, or other shapes. Whatever shape pilot hole forming members 272 may take, they may generally have pointed distal ends for piercing tissue or bone.

Similarly to insert 290, proximal head 271 may have connecting fins 277 extending lengthwise down insert 270 toward distal end 275. Connecting fins 277 may additionally have inward facing protrusions 279. As a user inserts insert 270 into sheath 203, inward facing protrusions 279 may slide into grooves 214, securing insert 270 to staple delivery device 200, as depicted in FIG. 19 with respect to insert 290.

Figure 24:
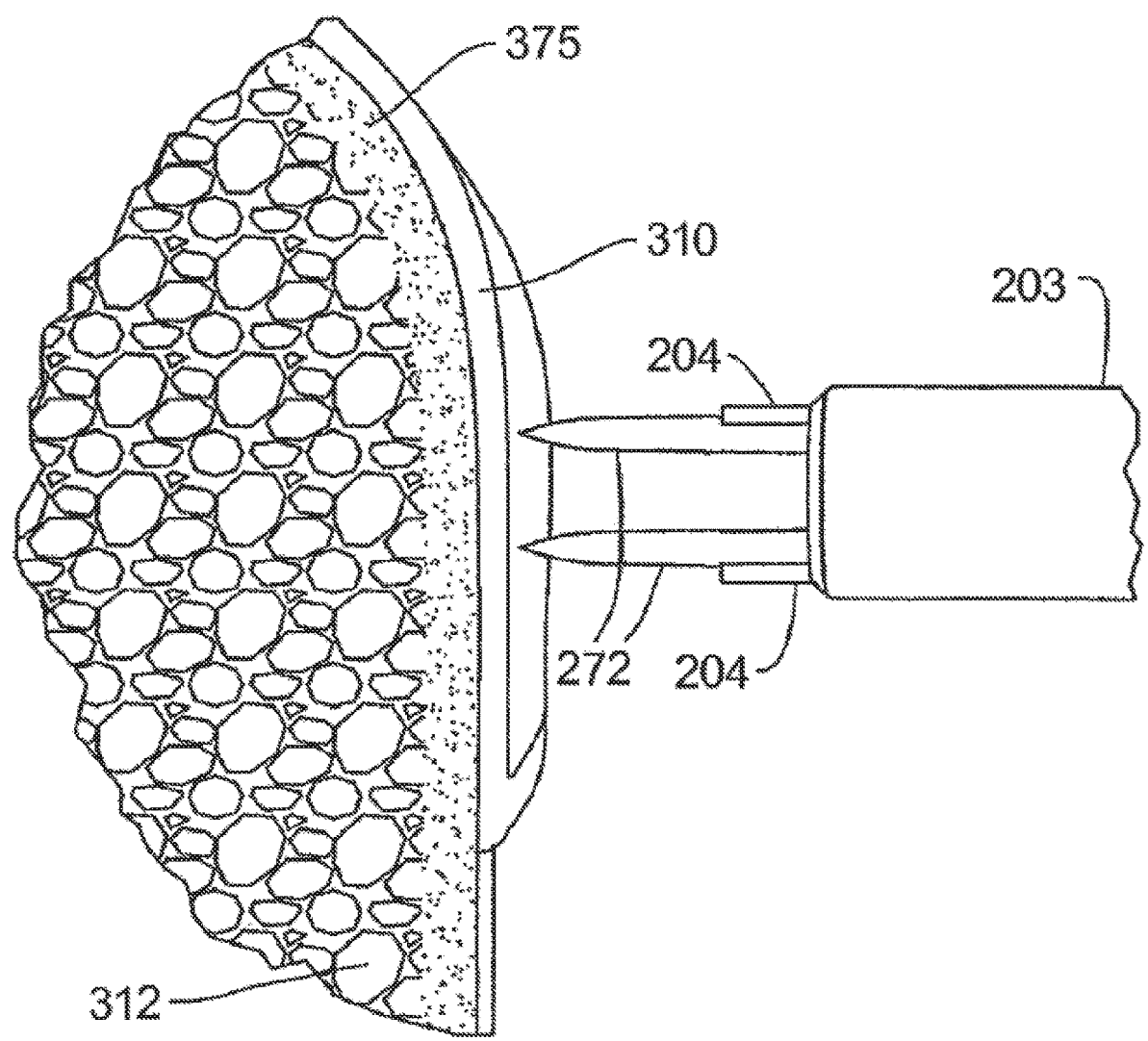
FIG. 24 is a cross section view depicting an example fastener delivery device in accordance with one example of the present disclosure positioned at an implant site.

A user may then position pilot hole forming members 272 at a location of the implant site adjacent to tissue or bone into which a staple will be deployed. FIG. 24 is a cross section illustration and depicts the implant site when sheath 203 with received insert 270 is positioned near the implant site. In FIG. 24, implant 310 can be seen positioned on top of patient tissue 312. Additionally, sheath 203 is positioned adjacent implant 310 and patient tissue 312 with pilot hole forming members 272 extending distally of position retention members 204.

Figure 25:
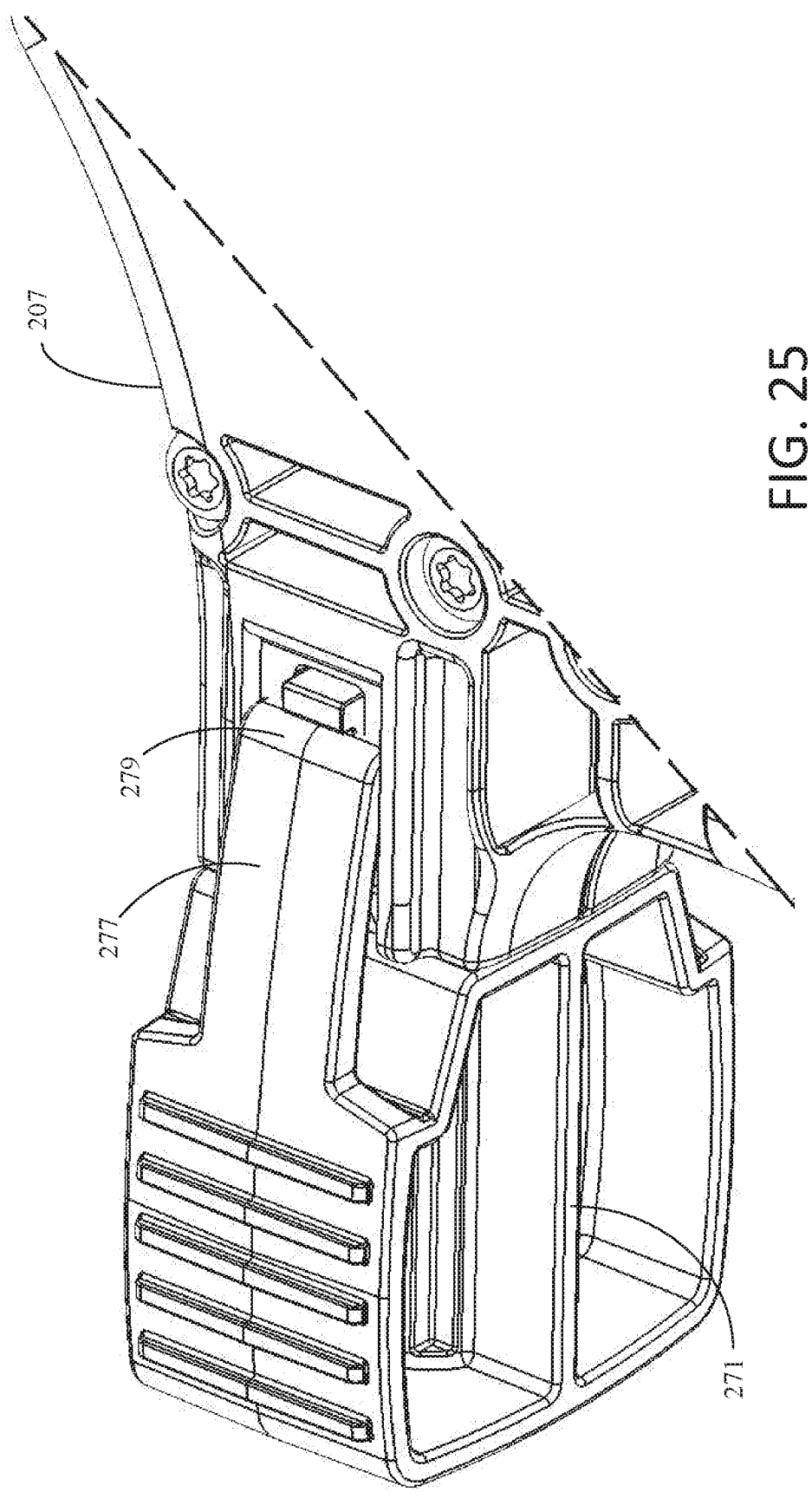
FIG. 25 is a schematic illustration depicting a proximal portion of an example fastener delivery device in accordance with one example of the present disclosure and a proximal head of an example insert when the insert is received within a sheath of the example fastener delivery device and after force has been applied to the proximal head to move the example insert in the distal direction.

Once the user has positioned pilot hole forming members 272 adjacent tissue or bone at the implant site, the user may apply force to proximal head 271 in the distal direction. As illustrated in FIGS. 19 and 20, when inward facing protrusions 299 are engaged with grooves 214, there remains a gap, gap 281, between proximal head 292 and housing 207. As illustrated in FIG. 25, a similar gap remains when inward facing protrusions 279 are engaged with grooves 214. As the user applies force to proximal head 271, inward facing protrusions 279 disengage with grooves 214 and insert 270 moves in the distal direction. As insert 270 moves in the distal direction, pilot hole forming members 272 positioned at the implant site are driven into the tissue or bone. FIG. 25 illustrates the position of proximal head 271 with respect to housing 207 when insert 270 has been advanced in the proximal direction as far as housing 207 will allow. As depicted, no gap exists between proximal head 271 and housing 207.

Figure 26:
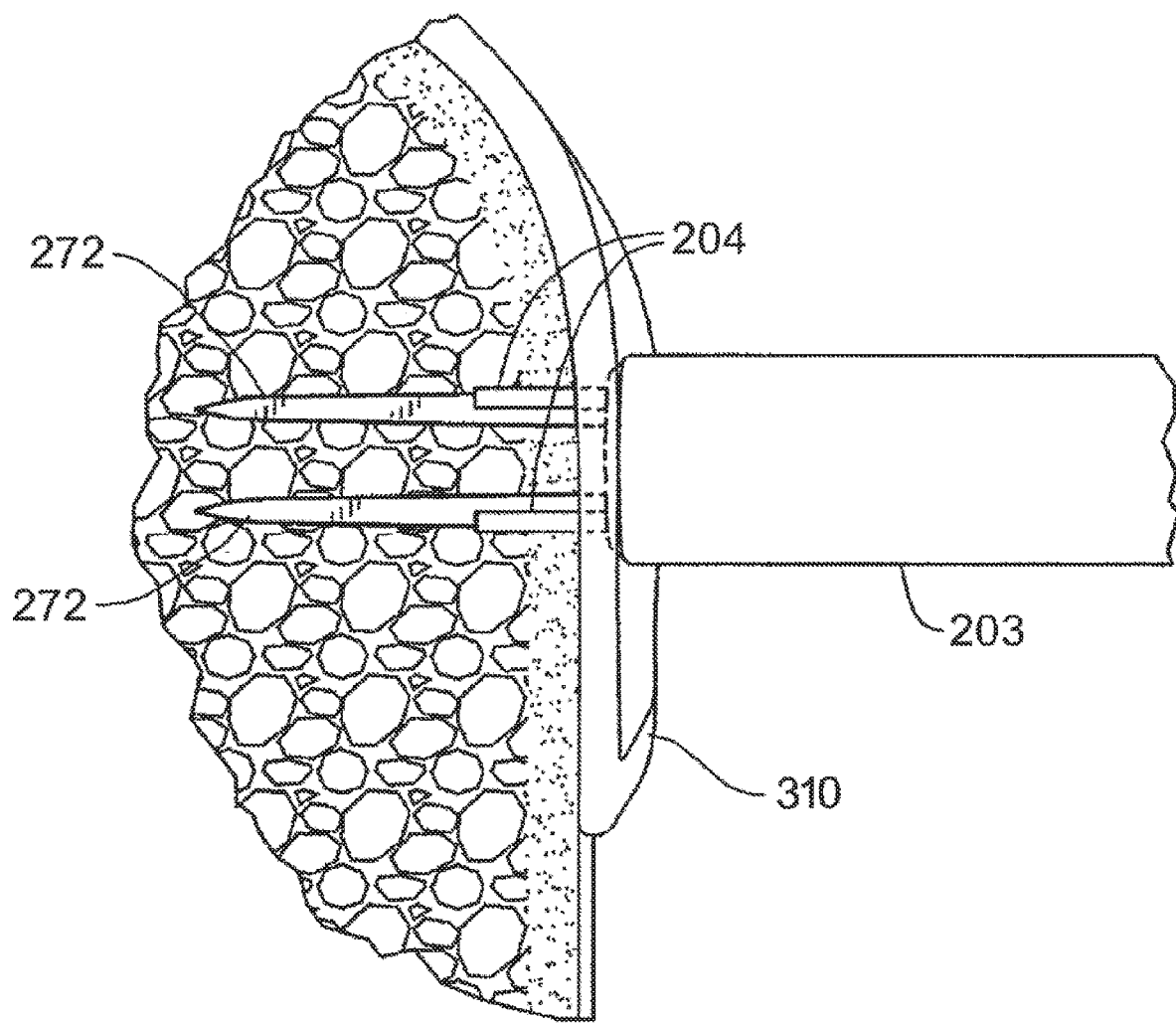
FIG. 26 is a cross section view depicting an example fastener delivery device in accordance with one example of the present disclosure positioned at an implant site after pilot hole forming members have been driven into tissue at the implant site.

FIG. 26 is another cross section illustration and depicts the position of pilot hole forming members 272 at the implant site when insert 270 has been advanced distally as far as housing 207 will allow. Pilot hole forming members can be seen extending through implant 310 and into patient tissue 312.

Another feature that staple delivery device may employ and can be seen in FIGS. 24 and 26 is the progressive disclosure of pilot hole forming members 272. That is, when inward facing protrusions 279 are engaged with grooves 214, pilot hole forming members 272 may extend distally at least partially beyond the distal end of position retention members 204. In some examples, in this initial position of proximal head 271 with respect to housing 207, pilot hole forming members 272 may extend between 0.05 inches (1.27 millimeters) and 0.35 inches (8.89 millimeters) beyond the distal end of position retention members 204, and in at least some examples, pilot hole forming members 272 may extend 0.083 inches (2.10 millimeters) beyond the distal end of position retention members 204. As force is applied to proximal head 271, and as insert 270 progresses distally, pilot hole forming members 272 extend progressively more beyond the distal end of position retention members 204. In FIG. 26, pilot hole forming members 272 are fully extended. In this position, pilot hole forming members 272 may extend between 0.4 inches (10.16 millimeters) and 0.65 inches (16.51 millimeters) beyond the distal end of position retention members 204. One advantage to examples that include this progressive disclosure feature is that having less length of pilot hole forming members 272 extending beyond position retention members 204 in the initial position may help prevent pilot hole forming members 272 from bending as force is applied to proximal head 271. In addition to driving pilot hole forming members 272 into tissue 312, the force applied to proximal head 271 may also drive position retention members 204 into tissue 312, as can be seen in FIG. 26.

Once the user has fully driven pilot hole forming members 272 into tissue 312, the user may remove insert 270. To remove insert 270, a user may squeeze trigger handle 205. The action of the internal components of staple delivery device 200 may cause insert connector 213A to push against proximal head 271 of insert 270. Although tissue 312 may be applying squeezing forces to pilot hole forming members 272 which work to retain pilot hole forming members 272 in tissue 312, the force multiplication action of staple delivery device 200, as described previously, may assist the user in removing pilot hole forming members 272 from tissue 312.

Figure 27:
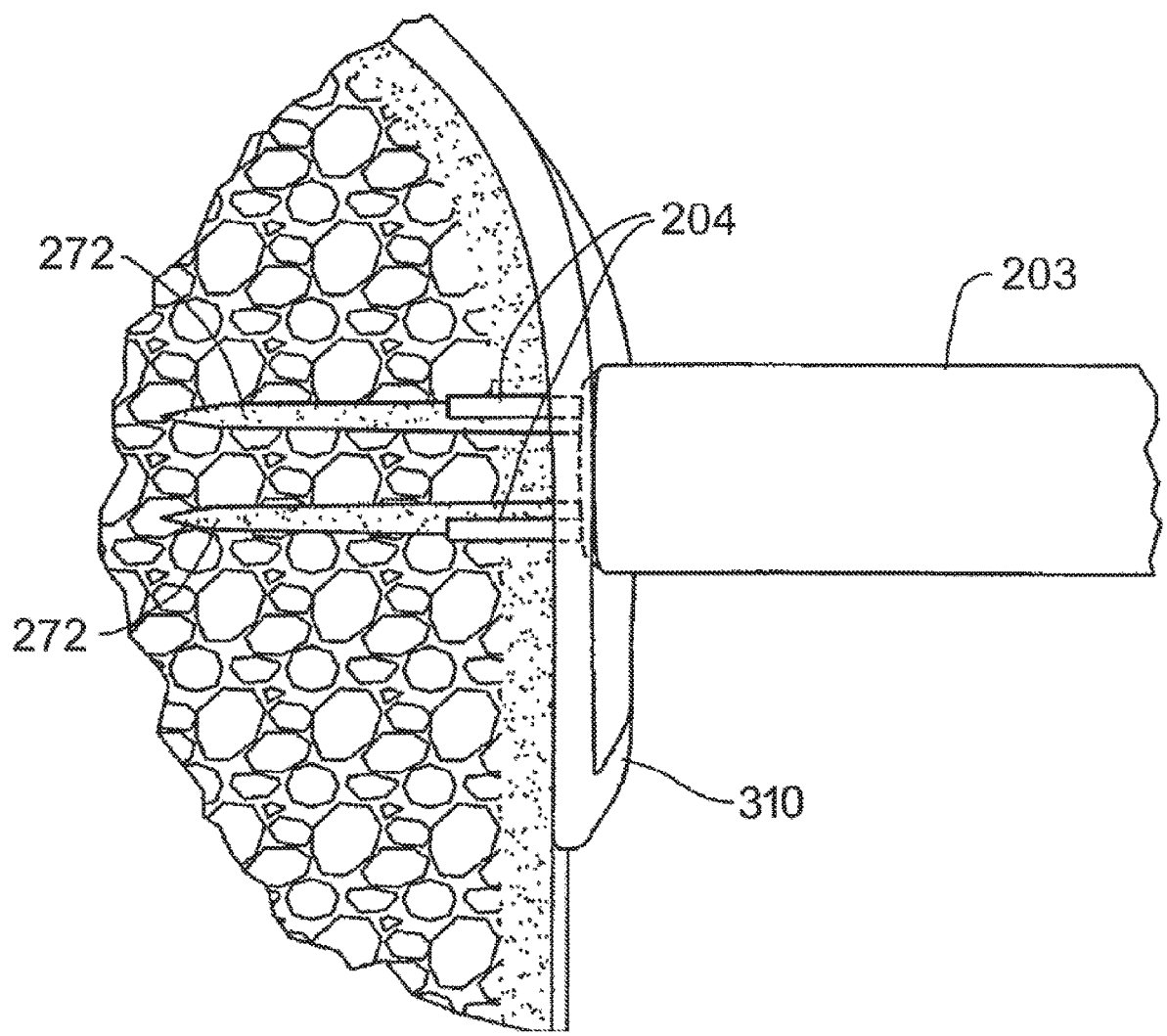
FIG. 27 is a cross section view depicting an example fastener delivery device in accordance with one example of the present disclosure positioned at an implant site after pilot hole forming members have been driven into and removed from tissue at the implant site.

FIG. 27 is another cross section illustration that depicts the implant area once insert 270 has been removed from staple delivery device 200. FIG. 27 illustrates that even after insert 270 has been removed, position retention members 204 may still remain in tissue 312. Position retention members 204 may act to maintain sheath 203 in position with respect to pilot holes 309 left by the pilot hole forming members 272.

Figure 28:
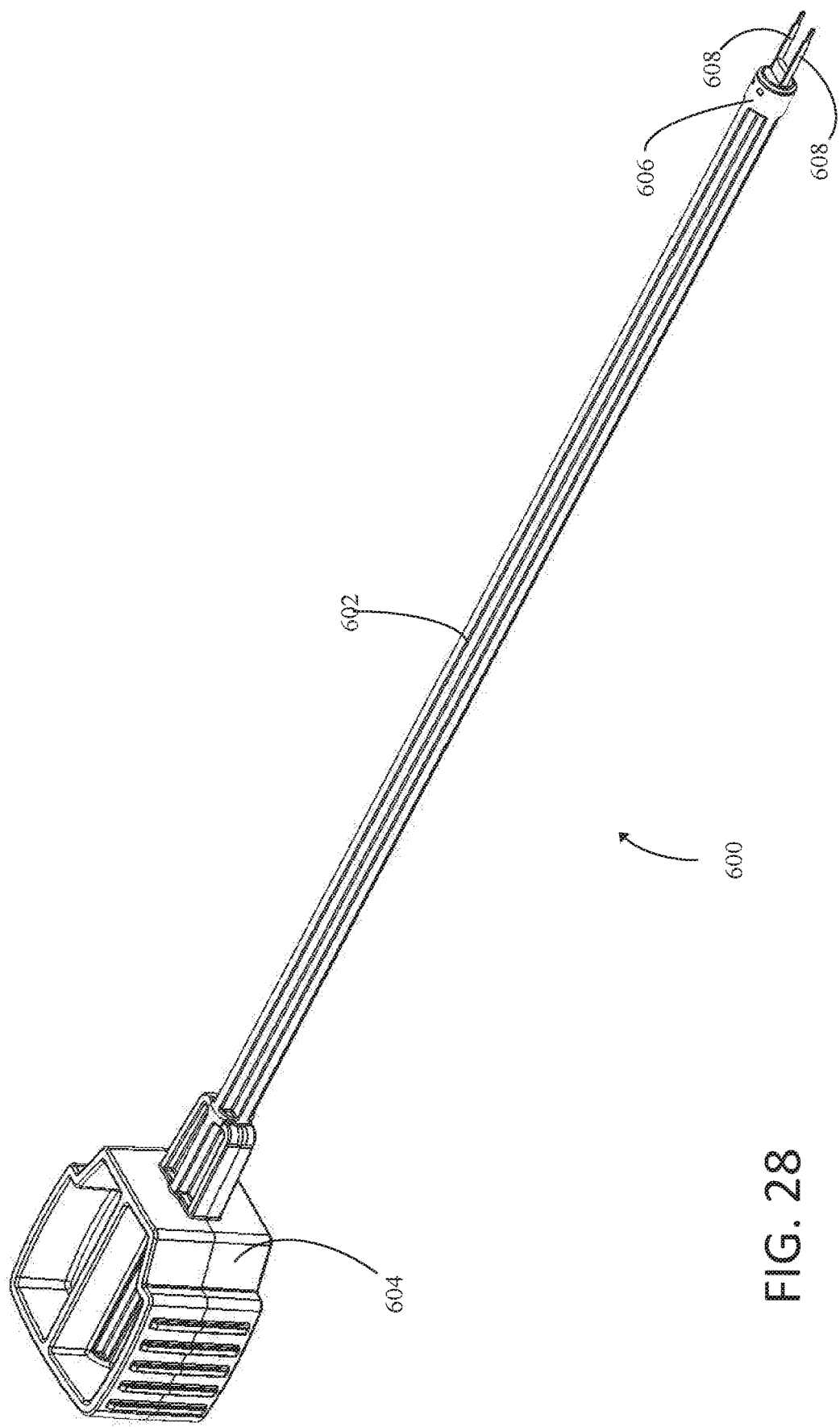
FIG. 28 is a schematic illustration depicting an example staple delivery insert in accordance with one example of the present disclosure.
Figure 29:
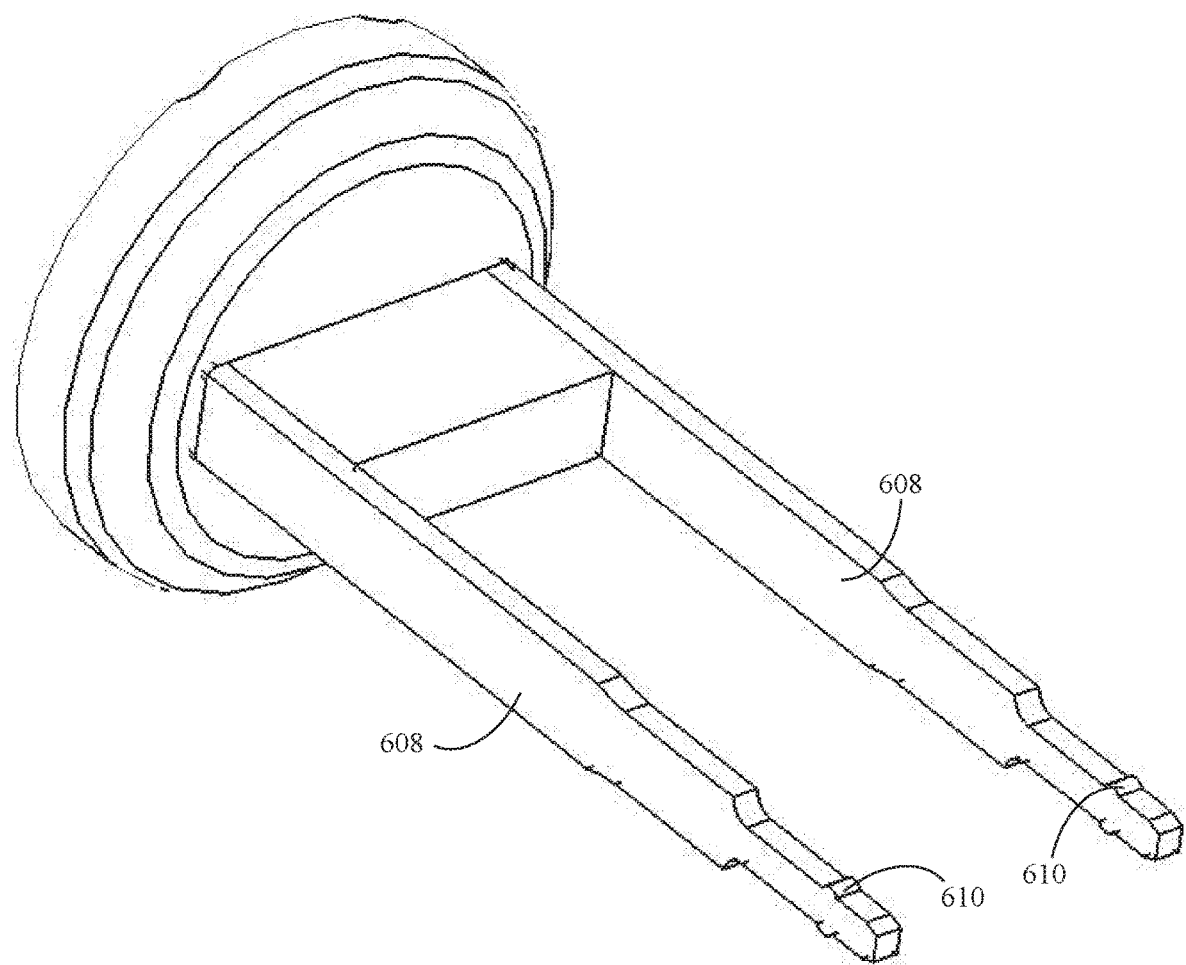
FIG. 29 is a schematic illustration of a distal portion of an example staple delivery insert in accordance with one example of the present disclosure.

Next, a user may insert staple delivery insert 600, as depicted in FIG. 28, into staple delivery device 200. Again, staple delivery insert 600 may generally be similar to inserts 290 and 270. For instance, insert 600 may be comprised of shaft 602, proximal head 604, and distal end 606. However, staple delivery insert 600 may have arms 608 connected to distal end 606 which may retain a staple, such as staple 100. In some examples, arms 608 may include detents 610, as illustrated in FIG. 29. Arms 608 may be designed to be received into cavities 128A, 128B of staple 100 and retain staple 100 with friction. For instance, when arms 608 are received within cavities 128A, 128B of staple 100, detents 610 may press against inner surfaces of cavities 128A, 128B, thereby retaining staple 100 to arms 608 by friction.

Once staple delivery insert 600 is received within sheath 203, a user may then apply force to the proximal end of staple delivery insert 600. The applied force may drive arms 610 of the staple delivery device, along with retained staple 100, into pilot holes 309. As discussed with respect to FIGS. 1-4, natural movement of tissue 312 and/or a pullout force applied to the bridge of staple 100 may act to secure staple 100 within tissue 312.

Figure 30:
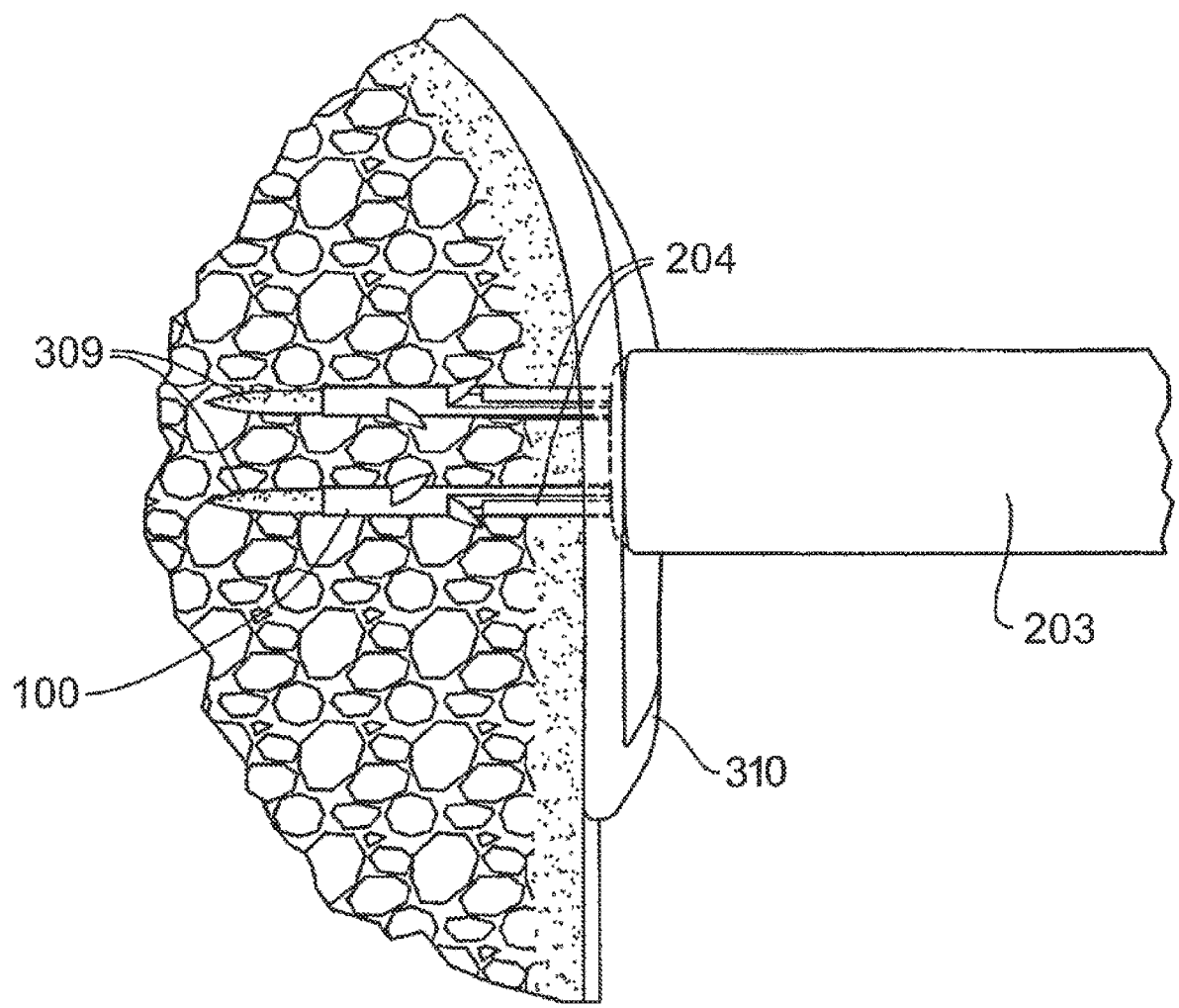
FIG. 30 is a cross section view depicting an example fastener delivery device in accordance with one example of the present disclosure positioned at an implant site after an example fastener has been deployed into pilot holes formed in tissue at the implant site.

The user may then remove staple delivery insert 600 from staple delivery device 200. Tissue 312 may impart a holding force on staple 100 sufficient to overcome the friction force between detents 610 on arms 608 of staple delivery insert 600 and staple 100 such that staple delivery insert 600 may be removed from tissue 312 while staple 100 remains in tissue 312, as depicted in FIG. 30.

Finally, the user may then retract staple delivery device 200 from the patient and finish the procedure to secure implant 310 to tissue 312 of the patient. This may include fixing staple 100 to a tendon of the patient with one or more fixation devices. Alternatively, implant 310 may have already been affixed to the tendon before affixing implant 310 to tissue 312.

In light of the above description, it should be understood that other examples of staple 100, staple delivery device 200, and inserts 290 and 270 that are still within the spirit and scope of the present disclosure may differ from the specific examples illustrated herein. For instance, in some examples, staple delivery device 200 and inserts 290 and 270 may not have a progressive disclosure feature. In such examples, grooves 214 may be positioned with respect to housing 207 such that when inward projecting members 299, 279 engage with groove 214, no gap is left between proximal head 292, 271 and housing 207. Additionally, in other examples, inserts 290 and 270 may be secured to housing 207 in a manner other than with inward projecting members 299, 279 and grooves 214.

Accordingly, it should be generally understood that even though numerous characteristics of various embodiments have been set forth in the foregoing description, together with details of the structure and function of various embodiments, this detailed description is illustrative only, and changes may be made in detail, especially in matters of structure and arrangements of parts illustrated by the various embodiments to the full extent indicated by the broad general meaning of the terms in which the appended claims are expressed.

What is claimed:

1. A fastener delivery tool comprising:
   a sheath assembly having a position retention member proximate a distal end of the sheath assembly, the position retention member being configured to maintain the position of the sheath assembly relative to tissue or bone;
   a handle assembly coupled to a proximal end of the sheath assembly, the handle assembly comprising a housing, a trigger handle, and an insert connector, and
   an insert removably insertable into a lumen of the sheath assembly from a proximal end of the housing of the handle assembly;
   wherein an external force applied to the trigger handle in a proximal direction causes displacement of the trigger handle relative to a rest position,
   wherein displacement of the trigger handle from the rest position within a first displacement range imparts a first amount of proximally directed force on the insert connector relative to the applied external force and displacement of the trigger handle from the rest position within a second displacement range imparts a second amount of proximally directed force on the insert connector relative to the applied external force, wherein the insert connector is configured to move the insert present within the lumen of the sheath assembly in a proximal direction in response to the applied external force, and
   wherein the first amount of proximally directed force is greater than the second amount of proximally directed force.

2. The fastener delivery tool of claim 1, further comprising a cam follower connected to the insert connector, and
   wherein the trigger handle imparts force on the insert connector through the cam follower when the trigger handle is displaced from the rest position.

3. The fastener delivery tool of claim 2, wherein the cam follower comprises a flat portion and a protrusion.

4. The fastener delivery tool of claim 3, wherein within the first displacement range, the cam follower protrusion contacts the trigger handle.

5. The fastener delivery tool of claim 3, wherein within the second displacement range, the cam follower flat portion contacts the trigger handle.

6. The fastener delivery tool of claim 1, wherein the first amount of proximally directed force is between two times and six times the applied external force.

7. The fastener delivery tool of claim 1, wherein the first amount of proximally directed force is four times the applied external force.

8. The fastener delivery tool of claim 1, wherein the second amount of proximally directed force is between one and four times the applied external force.

9. The fastener delivery tool of claim 1, wherein the first displacement range is greater than the second displacement range.

10. The fastener delivery tool of claim 1, wherein the fastener delivery tool further comprises a spring connected to the housing and the trigger handle, wherein the spring biases the trigger handle to the rest position.

11. A fastener delivery tool comprising:
    a sheath assembly comprising a lumen;
    a handle assembly coupled to a proximal end of the sheath assembly, the handle assembly comprising a housing and a trigger handle, and
    an insert removably insertable into the lumen of the sheath assembly from a proximal end of the housing of the handle assembly;
    wherein, when the insert is received within the lumen of the sheath assembly, proximal movement of the trigger handle relative to a rest position within a first movement range imparts a first amount of proximally directed force on the received insert, and wherein proximal movement of the trigger handle relative to the rest position within second movement range imparts a second amount of proximally directed force on the received insert, wherein the first amount of proximally directed force is greater than the second amount of proximally directed force.

12. The fastener delivery tool of claim 11, wherein the first movement range and the second movement range do not overlap.

13. The fastener delivery tool of claim 11, wherein the first movement range is greater than the second movement range.

14. The fastener delivery tool of claim 11, wherein the first amount of proximally directed force is between two times and five times the second amount of proximally directed force.

15. The fastener delivery tool of claim 11, wherein the first amount of proximally directed force is three times the second amount of proximally directed force.

16. A fastener delivery tool comprising:
a sheath assembly having a position retention member proximate a distal end of the sheath assembly, the position retention member being configured to maintain the position of the sheath assembly relative to tissue or bone;
a handle assembly coupled to a proximal end of the sheath assembly, the handle assembly comprising a housing, a trigger handle, and an insert connector, and
an insert removably insertable into a lumen of the sheath assembly from a proximal end of the housing of the handle assembly;
wherein an external force applied to the trigger handle in a proximal direction causes displacement of the trigger handle relative to a rest position,
wherein displacement of the trigger handle from the rest position within a first displacement range pushes the insert connector proximally relative to the housing and imparts a first amount of proximally directed force on the insert connector relative to the applied external force and displacement of the trigger handle from the rest position within a second displacement range pushes the insert connector proximally relative to the housing and imparts a second amount of proximally directed force on the insert connector relative to the applied external force,
wherein the insert connector is configured to move the insert present within the lumen of the sheath assembly in a proximal direction in response to the applied external force, and
wherein the first amount of proximally directed force is greater than the second amount of proximally directed force.

17. The fastener delivery tool of claim 16, further comprising a cam follower connected to the insert connector, and
wherein the trigger handle imparts force on the insert connector through the cam follower when the trigger handle is displaced from the rest position.

18. The fastener delivery tool of claim 17, wherein the cam follower comprises a first contact point and a second contact point spaced away from the first contact point;
wherein within the first displacement range, the first contact point contacts the trigger handle and the second contact point is spaced away from the trigger handle; and
wherein within the second displacement range, the second contact point contacts the trigger handle.

19. The fastener delivery tool of claim 18, wherein the first amount of proximally directed force is between two times and six times the applied external force and the second amount of proximally directed force is between one and four times the applied external force.

20. The fastener delivery tool of claim 19, wherein the first displacement range is greater than the second displacement range.

* * * * *